United States Patent
Kelly et al.

(10) Patent No.: US 11,541,030 B2
(45) Date of Patent: Jan. 3, 2023

(54) METHODS FOR THE TREATMENT OF INFLAMMATION ASSOCIATED WITH INFECTION

(71) Applicant: NOXOPHARM LIMITED, Gordon (AU)

(72) Inventors: Graham Kelly, Gordon (AU); Olivier Laczka, Gordon (AU); Michael Gantier, Gordon (AU)

(73) Assignee: NOXOPHARM LIMITED, Gordon (AU)

( * ) Notice: Subject to any disclaimer, the term of this patent is extended or adjusted under 35 U.S.C. 154(b) by 0 days.

(21) Appl. No.: 17/324,546

(22) Filed: May 19, 2021

(65) Prior Publication Data

US 2021/0299085 A1     Sep. 30, 2021

Related U.S. Application Data

(63) Continuation of application No. PCT/AU2021/050282, filed on Mar. 30, 2021.

(30) Foreign Application Priority Data

Mar. 30, 2020 (AU) ................. 2020900970

(51) Int. Cl.
| | | |
|---|---|---|
| *A61K 31/352* | (2006.01) | |
| *A61K 9/00* | (2006.01) | |
| *A61K 45/06* | (2006.01) | |
| *A61P 29/00* | (2006.01) | |

(52) U.S. Cl.
CPC .......... *A61K 31/352* (2013.01); *A61K 9/0019* (2013.01); *A61K 45/06* (2013.01); *A61P 29/00* (2018.01)

(58) Field of Classification Search
CPC .. A61K 31/522; A61K 31/404; A61K 31/513; A61K 31/517; A61K 31/5377; A61K 31/635; A61K 45/06; A61K 2300/00
See application file for complete search history.

(56) References Cited

U.S. PATENT DOCUMENTS

| | | | |
|---|---|---|---|
| 4,837,214 A | 6/1989 | Tanaka et al. | |
| 7,488,494 B2 | 2/2009 | Heaton et al. | |
| 2004/0152761 A1 | 8/2004 | Heaton et al. | |
| 2005/0049424 A1 | 3/2005 | Kelly et al. | |
| 2005/0154452 A1 | 7/2005 | Hezi-Yamit et al. | |
| 2006/0074127 A1 | 4/2006 | Heaton et al. | |
| 2006/0100238 A1 | 5/2006 | Kelly et al. | |
| 2006/0167037 A1 | 7/2006 | Kelly et al. | |
| 2006/0167083 A1* | 7/2006 | Kelly ................. | A61P 9/00 514/454 |
| 2006/0183728 A1 | 8/2006 | Kelly et al. | |
| 2007/0036834 A1 | 2/2007 | Pauletti et al. | |
| 2007/0196381 A1 | 8/2007 | Holt | |
| 2009/0028964 A1 | 1/2009 | Muni et al. | |
| 2009/0104235 A1 | 4/2009 | Heinrich | |
| 2009/0233999 A1 | 9/2009 | Heaton et al. | |
| 2010/0152284 A1 | 6/2010 | Brown et al. | |
| 2011/0166142 A1 | 7/2011 | Eiffe | |
| 2012/0039917 A1 | 2/2012 | Husband et al. | |
| 2016/0340329 A1 | 11/2016 | Heaton et al. | |
| 2019/0117618 A1 | 4/2019 | Kelly et al. | |
| 2019/0117620 A1 | 4/2019 | Kelly | |
| 2019/0160004 A1 | 5/2019 | Kelly | |

FOREIGN PATENT DOCUMENTS

| | | |
|---|---|---|
| WO | WO 1998/008503 | 3/1998 |
| WO | WO 2000/066576 | 11/2000 |
| WO | WO 2003/035635 | 5/2003 |
| WO | WO 2003/086386 | 10/2003 |
| WO | WO 2004/009035 | 1/2004 |
| WO | WO 2004/030662 | 4/2004 |
| WO | WO 2005/027842 | 3/2005 |
| WO | WO 2005/049008 | 6/2005 |
| WO | WO 2006/032086 | 3/2006 |
| WO | WO 2006/108212 | 10/2006 |
| WO | WO 2007/035515 | 3/2007 |
| WO | WO 2009/003229 | 1/2009 |
| WO | WO 2010/022467 | 3/2010 |
| WO | WO 2010/054438 | 5/2010 |
| WO | WO 2011/121418 | 10/2011 |
| WO | WO 2013/056217 | 4/2013 |

(Continued)

OTHER PUBLICATIONS

Puneet et al., Science, vol. 238, Jun. 4, 2010, 1290-1294 (Year: 2010).*
Kim et al., Oncogene (2014) 33, 3583-3593 (Year: 2014).*
Zhou et al., Lancet; 395: 1054-1062, published online Mar. 9, 2020. (Year: 2020).*
Noxopharm, Formulation Development, Market News & Trends, Noxopharm Phase 1 Clinical, copyright 2018 (Year: 2018).*
WHO (World Health Organization) Interim Guidance, Mar. 16, 2020, (Year: 2020).*
Hu et al., EbioMedicine, published by the Lancet, vol. 41, Mar. 2019, pp. 497-508 (Year: 2019).*
Dr. Cron, Don't Forget the Host: COVID-19 Cytokine Storm, Mar. 16, 2020. (Year: 2020).*
Benmerzoug et al., Nature Communications vol. 9, Article No. 5226 (2018) (Year: 2018).*

(Continued)

*Primary Examiner* — Jean P Cornet
(74) *Attorney, Agent, or Firm* — ParkerHighlander, PLLC.

(57) ABSTRACT

The present invention provides methods of treating inflammation associated with infection, and methods of preventing or reducing the severity of sepsis caused by inflammation associated with infection, in an individual comprising, consisting essentially of or consisting of the steps of administering a therapeutically effective amount of idronoxil, or derivative, pharmaceutically acceptable salt, ester, amide, polymorph and/or prodrug thereof to the individual, wherein the individual is diagnosed with, or suspected of having, early stage organ damage caused by inflammation associated with infection.

19 Claims, 18 Drawing Sheets

(56) References Cited

FOREIGN PATENT DOCUMENTS

| WO | WO-2013138800 A2 * | 9/2013 | ........... B01D 61/243 |
|---|---|---|---|
| WO | WO 2014/160130 | 10/2014 | |
| WO | WO 2015/069562 | 5/2015 | |
| WO | WO 2016/024231 | 2/2016 | |
| WO | WO 2016/028672 | 2/2016 | |
| WO | WO 2016/192680 | 12/2016 | |
| WO | WO 2017/025918 | 2/2017 | |
| WO | WO 2017/079746 | 5/2017 | |
| WO | WO 2017/173498 | 10/2017 | |
| WO | WO 2017/181242 | 10/2017 | |
| WO | WO 2018/111902 | 6/2018 | |
| WO | WO 2019/240871 | 12/2019 | |
| WO | WO 2019/240872 | 12/2019 | |
| WO | WO 2020/051644 | 3/2020 | |

OTHER PUBLICATIONS

Gill et al., Free Radic Biol Med. May 1, 2010; 48(9): 1121-1132 (Year: 2010).*

Zuo et al., Molecular Biology of the SARS-Coronavirus. Jul. 22, 2009 : 247-258 . . . (Year: 2009).*

"Idronoxil (Code C132257)," National Cancer Institute Thesaurus History, available online at https://ncit.nci.nih.gov/ncitbrowser/pages/concept_history.jsf?dictionary=NCI_Thesaurus&version=21.01d&code=C132257, accessed Mar. 4, 2021.

"Idronoxil (Code C2642)," National Cancer Institute Thesaurus History, available online at https://ncit.nci.nih.gov/ncitbrowser/pages/concept_history.jsf?dictionary=NCI_Thesaurus&version=21.01d&code=C2642, accessed Mar. 4, 2021.

Aguero et al., "Phenoxodiol inhibits growth of metastatic prostate cancer cells," The Prostate, 70(11):1211-1221, 2010.

Ahmad et al., "Perspectives on the Role of Isoflavones in Prostate Cancer", The AAPS Journal, 15(4):991-1000, 2013.

Ahmad et al., "Soy isoflavones in conjunction with radiation therapy in patients with prostate cancer," Nutrition and Cancer England, Taylor & Francis, US, 62(7):996-1000, 2010.

Ajazuddin et al., "Role of herbal bioactives as a potential bioavailability enhancer for Active Pharmaceutical Ingredients," Fitoterapia, 97:1-14, 2014.

Alvero et al., "Anti-tumor activity of phenoxodiol: from bench to clinic," Future Oncol., 4(4):475-482, 2008.

Anonymous, "Brain Cancer Study Commences," Feb. 1, 2017 (Feb. 1, 2017), pp. 1-3, XP55639769, Sydney, Australia Retrieved from the Internet: URL:https://www.noxopharm.com/site/PDF/11470/BrainCancerStudyCommences [retrieved on Nov. 6, 2019].

Anonymous: "Idronoxil suppository NOX66", NCI Drug Dictionary, XP009514254. Retrieved from the Internet <URL:https://www.cancer.gov/publications/dictionaries/cancer-drug/def/idronoxil-suppository-nox66> on May 2, 2017.

Bandara et al., "Topical isoflavonoids reduce experimental cutaneous inflammation in mice," Immunology and Cell Biology, 88(7):727-733, 2010.

Baviskar et al., "Drug delivery on rectal absorption: Suppositories," International Journal of Pharmaceutical Sciences Review and Research, 21(1):70-76, 2013.

Block et al., "Immune System Effects of Echinacea, Ginseng, and Astragalus: A Review," Integrative Cancer Therapies, 2(3):247-267, 2003.

Budman et al., "Identification of unique synergistic drug combinations associated with down expression of surviving in a preclinical breast cancer model system," Anticancer Drugs, 23(2):272-279, 2012.

Burkard et al., "Dietary flavonoids and modulation of natural killer cells: implications in malignant and viral diseases," Journal of Nutritional Biochemistry 46:1-12, 2017.

Chakravarty et al., "Flt3L Therapy following Localized Tumor Irradiation Generates Long-Term Protective Immune Response in Metastatic Lung Cancer: Its Implication in Designing a Vaccination Strategy," Oncology, 70:245-254, 2006.

Cho et al., "Does Radiotherapy for the Primary Tumor Benefit Prostate Cancer Patients with Distant Metastasis at Initial Diagnosis?" PLOS ONE, 11(1):e0147191, 12 pages, 2016.

Choueiri et al., "Phase I trial of phenoxodiol delivered by continuous intravenous infusion in patients with solid cancer," Annals of Oncology, 17:860-865, 2006.

Cremer Health, "Witepsol," Retrieved on Sep. 27, 2019. Retrieved from the internet <URL: https://www.pharmacompass.com/pAssets/pdf/edqm/application/witepsol.pdf>; pp. 1-44. (Year: 2019).

Database WPI Week Apr. 2012 Thomson Scientific, London, GB; AN 2011-B25102 & KR 2011 0004525 A (Univ Dong Eui Ind Academic Coop Found), 2009.

Diomina, "Classification, nomenclature, and brief description of suppository bases," Development and Registration of Medicinal Products, 2(15):1-10, 2016. (English abstract and English translation of Table 1 of Russian publication).

Fisher et al., "The effect of phospholipid structure on the thermal stability of rhodopsin," Biochemica et Biophysica Acta, 707(2):273-279, 1982.

Georgaki, et al., "Phenoxodiol, an anticancer isoflavene, induces immunomodulatory effects in vitro and in vivo," Journal of Cellular and Molecular Medicine, 13(9B):3929-3938, 2009.

Gruca et al., "Synthetic genistein glycosides inhibiting EGFR phosphorylation enhance the effect of radiation in HCT 116 colon cancer cells," Molecules, 19(11):18558-18573, 2014.

Herst et al., "The antiproliferative effects of phenoxodiol are associated with inhibition of plasma membrane electron transport in tumour cell lines and primary immune cells," Biochemical Pharmacology 74:1587-1595, 2007.

Howes et al., "Pharmacokinetic of phenoxodiol, a novel isoflavone, following intravenous administration to patients with advanced cancer," BMC Clinical Pharmacology, 11(1):1-8, 2011.

Kang et al., "Advances in drug delivery system for platinum agents based combination therapy," Cancer Biol. Med., 12:362-374, 2015.

Kim et al., "Genistein decreases cellular redox potential, partially suppresses cell growth in HL-60 leukemia cells and sensitizes cells toy-radiation-induced cell death," Molecular Medicine Reports, 10(6):2786-2792, 2014.

Liao et al., "Interleukin-2 at the Crossroads of Effector Responses, Tolerance, and Immunotherapy," Immunity, 38(1):13-25, 2013.

Lipp and Anklam, "Review of cocoa butter and alternative fats for use in chocolate—Part A. Compositional data," Food Chemistry, 62(1):73-97, 1998.

Lock et al., "Abscopal Effects: Case Report and Emerging Opportunities," Cureus, 7(10):e344, 2015.

Ludgate, "Optimizing cancer treatments to induce an acute immune response: radiation Abscopal effects, PAMPs, and DAMPs," Clinical Cancer Research, 18(17):4522-4525, 2012.

Mahoney et al., "Cytotoxic effects of the novel isoflavone, phenoxodiol, on prostate cancer cell lines," J. Biosci., 37(1):73-84, 2012.

McPherson et al., "Enhancement of the activity of phenoxodiol by cisplatin in prostate cancer cells," British Journal of Cancer, 100(4):649-655, 2009.

Morré et al., "ECTO-NOX Target for the Anticancer Isoflavone Phenoxodiol," Oncology Research, 16:299-312, 2007.

National Cancer Institute, "Idronoxil", NCI Drug Dictionary [online], retrieved from https://www.cancer.gov/publications/dictionaries/cancer-drug/search/idronoxil/?searchMode=Begins on May 25, 2021.

Noxopharm Limited, "Phase Ia/Ib and Potential Phase IIa Study of the Safety and Pharmacokinetics of NOX66 Both as a Monotherapy and in Combination with Carboplatin in Patients with Refractory Solid Tumours," ClinicalTrials.gov archive [online] NCT02941523 on Oct. 20, 2016, retrieved from https://clinicaltrials.gov/archive/NCT02941523/2016_10 20, on May 2, 2017.

PCT International Search Report and Written Opinion issued in International Application No. PCT/AU2017/050300, dated May 24, 2017.

PCT International Search Report and Written Opinion issued in International Application No. PCT/AU2017/050299, dated May 24, 2017.

PCT International Search Report and Written Opinion issued in International Application No. PCT/AU2017/050363, dated May 25, 2017.

(56) References Cited

OTHER PUBLICATIONS

PCT International Search Report and Written Opinion issued in International Application No. PCT/AU2017/050301, dated May 25, 2017.
PCT International Search Report and Written Opinion issued in International Application No. PCT/AU2016/050674, dated Aug. 31, 2016.
PCT International Search Report and Written Opinion issued in International Application No. PCT/AU2021/050282, dated Apr. 21, 2021.
PCT International Search Report and Written Opinion issued in International Application No. PCT/AU2020/050730, dated Aug. 27, 2020.
Perez, "Carboplatin in combination therapy for metastatic cancer," The Oncologist, 9:518-52, 2004.
Pinato et al., "Evolving concepts in the management of drug resistant ovarian cancer: Dose dense chemotherapy and the reversal of clinical platinum resistance," Cancer Treat. Rev., http://dx.doi.org/10.1016/j.ctrv.2012.04.004. 8 pages. 2012.
Postow et al., "Immunologic Correlates of the Abscopal Effect in a Patient with Melanoma," N. Engl. J. Med., 366:925-31, 2012.
Raffoul et al., "Radiosensitization of prostate cancer by soy isoflavones," Current Cancer Drug Targets, 7(8):759-765, 2007.
Reynders et al., "The abscopal effect of local radiotherapy: using immunotherapy to make a rare event clinically relevant," Cancer Treat. Rev., 41(6): 503-510, 2015.
Royal North Shore Hospital, "Phase I Study of Idronoxil Combined with Radiation Treatment in Men with Metastatic Prostate Cancer," ClinicalTrials.gov archive [online], NCT03041285 on Feb. 1, 2017, retrieved from https://clinicaltrials.gov/archive/NCT03041285/2017 02 _ 01 on May 2, 2017.
Saif et al., "Flavonoids, phenoxodiol, and a novel agent, triphendiol, for the treatment of pancreaticobiliary cancers," Expert Opinion Investigational Drugs, 18(4):469-79, 2009.
Shin et al., "Sensitization of the apoptotic effect of gamma-irradiation in genistein-pretreated CaSki cervical cancer cells," Journal of Microbiology & Biotechnology, 18(3):523-531, 2008.
Temozolomide prescription information, Feb. 2011 (Year: 2011).
Tonekaboni et al., "Predictive approaches for drug combination discovery in cancer," Briefings in Bioinformatics, 19(2):263-276, 2018.
Wang et al., "Prostate Cancer Treatment is Enhanced by Genistein In Vitro and In Vivo in a Syngeneic Orthotopic Tumor Model," Radiation Research, vol. 166, No. 1, Jul. 1, 2006 (Jul. 1, 2006), pp. 73-80, XP55626642, us ISSN: 0033-7587, DOI: 10.1667/RR3590.1.
Widyarini et al., "Isoflavonoid Compounds from Red Clover (*Trifolium pratense*) Protect from Inflammation and Immune Suppression Induced by UV Radiation," Photochemistry and Photobiology, 74(3):465-470, 2001.
Yasuda et al., "Intratumoral injection of interleukin-2 augments the local and abscopal effects of radiotherapy in murine rectal cancer," Cancer Sci., 102(7):1257-1263, 2011.
Yaylaci et al., "Phenoxodiol sensitizes metastatic colorectal cancer cells to f-fluorouracil and oxaliplatin-induced apoptosis through intrinsic pathway," EXCLI Journal, 19:936-949, 2000.
Yossepowitch et al., "Secondary Therapy, Metastatic Progression, and Cancer-Specific Mortality in Men with Clinically High-Risk Prostate Cancer Treated with Radical Prostatectomy," European Urology, 53(5):950-959, 2008.
Park et al., "The effect of radiation on the immune response to cancer," Int. J. Mol. Sci., 15:927-943, 2014.
Nakaya et al., "Potential for immunotherapy combined with cytotoxic chemotherapy/radiotherapy," *Journal of Molecular Targeted Therapy for Cancer*, 13(4):24-28, 2015. (English translation of Japanese publication).
Suzuki et al., "Significance of radiation-induced bystander effects in radiation therapy," *Jpn. J. Med. Phys.*, 34(2):70-78, 2014. (English translation of Japanese publication).
Bastard et al., "Autoantibodies against type I IFNs in patients with life-threatening COVID-19," *Science*, 370(423), 13 pages, 2020.
Bastard et al., "Autoantibodies neutralizing type I IFNs are present in ~ 4% of uninfected individuals over 70 years old and account for ~ 20% of COVID-19 deaths," *Sci. Immunol.*, 6(62): eab14340, 30 pages, 2021.
McNab et al., "Type I interferons in infectious diseases," *Nat. Rev. Immunol.*, 15(2):87-103, 2015.
Rackov et al., "The Role of IFN-$\beta$ during the Course of Sepsis Progression and its Therapeutic Potential," *Frontiers in Immunology*, 8(493), 8 pages, 2017.
Tate et al., "Reassessing the role of the NLRP3 inflammasome during pathogenic influenza A virus infection via temporal inhibition," *Scientific Reports*, 6:27912, 8 pages, 2016.
Yang et al., "IL-6 ameliorates acute lung injury in influenza virus infection," *Scientific Reports*, 7:43829, 11 pages, 2017.
Bliss GVS Pharma Limited, "Advantages and Disadvantages of Suppositories/Pessaries or Rectal/Vaginal Route of Drug Administration," Dec. 26, 2016. Retrieved from the internet on Nov. 3, 2021 from http://www.blissgvs.com/2016/12/26/advantages-and-disadvantages-of-suppositoriespessaries-or-rectalvaginal-route-of-drug-administration/.
Marin-Acevedo et al., "Next Generation of immune checkpoint therapy in cancer: new developments and challenges," *Journal of Hematology & Oncology*, 11:39, 20 pages, 2018.
Souza et al., "Phase 1 and pharmacokinetic study of weekly NV06 (Phenoxodiol™), a novel isoflav-3-ene, in patients with advanced cancer" *Cancer Chemother. Pharmacol.*, 58:427-433, 2016.
Haywood and Glass, "Compounding for analgesia," *Australian Pharmacist*, 29(1):45-48, 2010.

\* cited by examiner

METHODS FOR THE TREATMENT OF INFLAMMATION ASSOCIATED WITH INFECTION

CROSS REFERENCE(S) TO RELATED APPLICATIONS

This application is a continuation of International Application No. PCT/AU2021/050282, filed Mar. 30, 2021, which claims priority from Australian Provisional Application No. 2020900970, filed Mar. 30, 2020. The entire contents of each of which are incorporated herein by reference.

FIELD OF THE INVENTION

The present invention relates to compositions and methods for the treatment of inflammation associated with infection.

BACKGROUND OF THE INVENTION

Sepsis is a disease characterized by an overwhelming systemic inflammatory response to infection.

Bacterial sepsis is a complex systemic inflammatory syndrome caused by aggressive bacterial infection in the blood. Sepsis causes high morbidity and mortality in humans and other animals. In the United States, sepsis is a leading cause of nosocomial death for humans (particularly in intensive care units) and death from infections in young livestock and other animals. Each year, over 700,000 new cases of sepsis are diagnosed in humans. Extrapolated to a global population, this represents several million cases of severe sepsis worldwide annually. Mortality rates range from about 20-30% and represent at least 150,000 deaths per year in the United States.

Sepsis can result from many causes but is typically triggered by events such as pneumonia, other infections, trauma, surgery, and burns or by conditions such as cancer or AIDS. Sepsis usually begins with tremor, fever, falling blood pressure (septic shock), rapid breathing, rapid heart rate, and skin lesions. Within hours, sepsis may cause spontaneous clotting in blood vessels, severe hypotension, multiple organ failure, shock, and eventually death.

Typically, these symptoms are caused by the excessive or uncontrolled activation of host defense mechanisms such as cytokines, leukocytes, and complement. Certain symptoms, including clotting, are caused by the STING pathway, independent of cytokines.

Sepsis is usually caused by bacterial infections (either Gram-negative or Gram-positive bacteria) but can also be caused by other pathogens such as fungi, viruses, and parasites and non-infective stimuli such as superantigens. Most often however, sepsis is caused by Gram-negative bacterial infections. However, the injury and symptoms attributable to sepsis are not only caused by the bacteria but are also caused by a component of the bacterial cell wall known as endotoxin or lipopolysaccharide (LPS). LPS molecules are glycolipids that are ubiquitous in the outer membrane of all Gram-negative bacteria. While the known chemical structure of the LPS molecule is complex and diverse, a common feature is the lipid A region. Recognition of the highly conserved lipid A LPS region initiates many, if not all, of the events responsible for sepsis. LPS is released when the immune system destroys the invading bacteria.

There is a need for improved methods for treating inflammation associated with infection and for preventing sepsis.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect, the present invention provides a method of treating inflammation in an individual comprising, consisting essentially of or consisting of the steps of:
administering a therapeutically effective amount of idronoxil, or derivative, pharmaceutically acceptable salt, ester, amide, polymorph and/or prodrug thereof to the individual;
wherein the individual is diagnosed with, or suspected of having, early stage organ damage caused by inflammation associated with infection,
thereby treating the inflammation.

In another aspect, the present invention provides a method for the treatment of inflammation in an individual comprising, consisting essentially of or consisting of the steps of:
identifying a subject having, or suspected of having, early stage organ damage caused by inflammation associated with an infection; and
administering to the individual in need thereof a therapeutically effective amount of idronoxil, or derivative, pharmaceutically acceptable salt, ester, amide, polymorph and/or prodrug thereof,
thereby treating the inflammation in the individual.

In another aspect, the present invention provides a method of treating inflammation in an individual comprising, consisting essentially of or consisting of the steps of:
administering a therapeutically effective amount of idronoxil, or derivative, pharmaceutically acceptable salt, ester, amide, polymorph and/or prodrug thereof to the individual;
wherein administration is prior to late stage organ damage caused by inflammation associated with infection,
thereby treating the inflammation.

In another aspect, the present invention provides a method for the treatment of inflammation in an individual comprising, consisting essentially of or consisting of the steps of:
identifying a subject having, or suspected of having, inflammation associated with an infection, wherein the inflammation is characterised as prior to late stage organ damage caused by inflammation; and
administering to the individual in need thereof a therapeutically effective amount of idronoxil, or derivative, pharmaceutically acceptable salt, ester, amide, polymorph and/or prodrug thereof,
thereby treating the inflammation in the individual.

In any aspect, the inflammation associated with infection may be caused by, induced by or result from the infection.

In certain embodiments, the methods, uses or compositions of the invention find utility in treating or minimising the severity of a symptom of early stage organ damage caused by inflammation associated with infection.

In another aspect, the present invention also provides a method of treating, or reducing the severity of a symptom of early stage organ damage caused by inflammation associated with infection in an individual, the method comprising, consisting essentially of or consisting of administering to the individual in need thereof a therapeutically effective amount of idronoxil, or derivative, pharmaceutically acceptable salt, ester, amide, polymorph and/or prodrug thereof, thereby treating, or reducing the severity of a symptom of early stage organ damage in the individual.

In another aspect, the invention provides a method for the treatment or reduction of the severity of a symptom of early stage organ damage caused by inflammation associated with infection in an individual comprising, consisting essentially of or consisting of the steps of:

identifying a subject having, or suspected of having, early stage organ damage caused by inflammation associated with infection; and administering to the individual in need thereof a therapeutically effective amount of idronoxil, or derivative, pharmaceutically acceptable salt, ester, amide, polymorph and/or prodrug thereof, thereby treating, or reducing the severity of a symptom of early stage organ damage in the individual.

In certain preferred embodiments, the symptom of early stage organ damage is selected from: abnormal levels of one or more cytokines or inflammatory biomarkers, abnormal levels of clotting factors, abnormal levels of troponin I, abnormal levels of alanine aminotransferase, abnormal levels of blood urea nitrogen, abnormal levels of creatinine, abnormal levels of procalcitonin, abnormal levels of lactic dehydrogenase, elevated body temperature, elevated heart rate, elevated respiratory rate, abnormal lymphocyte cell count, abnormal neutrophil cell count, abnormal platelet cell count, low blood pressure, hypoxemia, tissue hypoxia, hypoperfusion, redness and swelling around a wound, low urine volume, dizziness or faintness, pale, discoloured or mottled skin, slurred speech, rigors, malaise, fatigue, anorexia, myalgia, arthralgia, nausea, vomiting, headache, rash, vomiting, diarrhoea, widened pulse pressure, increased cardiac output (early), potentially diminished cardiac output (late), hypofibrinogenemia ±bleeding, azotemia, transaminitis, hyperbilirubinemia, mental status changes, confusion, delirium, word finding difficulty or frank aphasia, hallucinations, tremor, dysmetria, altered gait, seizures and combinations thereof. Preferably, the individual is identified as having, or suspected of having, at least 2, 3, 4, 5, or 6 symptoms of early stage organ damage.

The one or more cytokines or inflammatory biomarkers may be selected from: interleukin-1 alpha (IL-1α) and interleukin-1β (IL-1β) (hereinafter collectively referred to as interleukin-1 or IL-1), interleukin-6 (IL-6), interleukin-8 (IL-8), interleukin-11 (IL-11), interleukin-12 (IL-12), interleukin-17 (IL-17), interleukin-18 (IL-18), interleukin-37 (IL-37), IP-10, tumour necrosis factor-alpha (TNF-α), interferon-gamma (IFN-γ), granulocyte-macrophage colony stimulating factor (GM-CSF), transforming growth factor-beta (TGF-β), interleukin-2 receptor (IL-2R), interleukin-4 (IL-4), interleukin-10 (IL-10), interleukin-13 (IL-13), interferon-alpha (IFN-α), interferon-beta (IFN-β), monocyte chemoattractant protein-1 (MCP-1 or CCL2), procalcitonin (PCT), C-reactive protein (CRP), C-C Motif Chemokine Ligand 5 (CCL5 or RANTES), β-2-microglobulin (β-2M), serum ferritin, D-dimer, cyclic guanosine monophosphate-adenosine monophosphate (cGAMP), and combinations thereof. More preferably, the one or more cytokines or inflammatory biomarkers may be selected from: IL-1β, IL-2R, IL-6, IL-8, IL-10, IL-12, IP-10, TNF-α, MCP-1, PCT, CRP, β-2M, serum ferritin, D-dimer, cGAMP, CCL5 (RANTES), IFN-α, IFN-β, IFN-γ and combinations thereof. Even more preferably, the one or more cytokines or inflammatory biomarkers may be selected from: IL-6, IP-10, PCT, CRP, D-dimer, and combinations thereof. Preferably, the individual is identified as having abnormal levels of at least 2, 3, 4, 5, or 6 cytokines or inflammatory biomarkers.

In another aspect, the invention also provides a method of alleviating or ameliorating a symptom of early stage organ damage caused by inflammation associated with infection in an individual in need thereof, the method comprising, consisting essentially of or consisting of administering to the individual in need thereof a therapeutically effective amount of idronoxil, or derivative, pharmaceutically acceptable salt, ester, amide, polymorph and/or prodrug thereof, thereby alleviating or ameliorating a symptom of early stage organ damage in the individual.

In another aspect, the invention provides a method for alleviating or ameliorating a symptom of early stage organ damage caused by inflammation associated with infection in an individual comprising, consisting essentially of or consisting of the steps of:

identifying a subject having, or suspected of having, early stage organ damage caused by inflammation associated with infection; and administering to the individual in need thereof a therapeutically effective amount of idronoxil, or derivative, pharmaceutically acceptable salt, ester, amide, polymorph and/or prodrug thereof, thereby alleviating or ameliorating a symptom of early stage organ damage in the individual.

In another aspect, the present invention also provides a method for inhibiting or minimising the progression of a symptom of early stage organ damage caused by inflammation associated with infection in an individual comprising, consisting essentially of or consisting of the steps of:

administering a therapeutically effective amount of idronoxil, or derivative, pharmaceutically acceptable salt, ester, amide, polymorph and/or prodrug thereof to an individual who is experiencing a symptom of early stage organ damage caused by inflammation associated with infection;

thereby inhibiting or minimising the progression of a symptom of early stage organ damage in the individual.

An individual may be identified as experiencing a symptom of early stage organ damage by any biochemical or clinical method or test as described herein.

In other embodiments, the methods, uses or compositions of the invention find utility in preventing or reducing the severity of sepsis caused by inflammation associated with infection.

In a further aspect, the invention thus provides a method of preventing or reducing the severity of sepsis caused by inflammation associated with infection comprising, consisting essentially of or consisting of the steps of:

identifying a subject having, or suspected of having, early stage organ damage caused by inflammation associated with infection wherein the subject is at risk of developing sepsis; and administering to the individual in need thereof a therapeutically effective amount of idronoxil, or derivative, pharmaceutically acceptable salt, ester, amide, polymorph and/or prodrug thereof, thereby preventing or reducing the severity of sepsis in the individual.

In a further aspect, the invention provides a method of preventing or reducing the severity of sepsis caused by inflammation associated with infection comprising, consisting essentially of or consisting of the steps of:

identifying a subject having, or suspected of having, inflammation, wherein;

the inflammation is characterised as prior to late stage organ damage caused by inflammation; and the subject is at risk of developing sepsis; and
administering to the individual in need thereof a therapeutically effective amount of idronoxil, or derivative, pharmaceutically acceptable salt, ester, amide, polymorph and/or prodrug thereof,
thereby preventing or reducing the severity of sepsis in the individual.

The individual may be identified as being at high, moderate, or low risk of developing sepsis caused by inflammation associated with infection.

In another embodiment, idronoxil, or derivative, pharmaceutically acceptable salt, ester, amide, polymorph and/or prodrug thereof, is administered starting at, or about 7-10 days from the onset of infection, or inflammation associated with infection, wherein the infection is caused by SARS-CoV-2. In this embodiment, the individual may be:
  suspected of having, or diagnosed as having early stage organ damage caused by inflammation associated with infection, or a symptom thereof; and/or
  identified as high risk for developing late stage organ damage or sepsis caused by inflammation associated with infection.

In another aspect, the present invention therefore also provides a method of treating inflammation associated with infection, or a symptom thereof, in an individual comprising, consisting essentially of, or consisting of the steps of:
  administering a therapeutically effective amount of idronoxil, or derivative, pharmaceutically acceptable salt, ester, amide, polymorph and/or prodrug thereof to the individual starting at, or about 7-10 days from the onset of infection, or inflammation associated with infection, wherein the infection is caused by SARS-CoV-2;
  thereby treating the inflammation, or symptom thereof, in the individual.

The individual may be diagnosed with, or suspected of having, early stage organ damage caused by the inflammation associated with infection, or a symptom thereof.

In another aspect, the present invention provides a method of treating an individual with idronoxil, or derivative, pharmaceutically acceptable salt, ester, amide, polymorph and/or prodrug thereof, the method comprising, consisting essentially of, or consisting of the steps of:
  providing an individual who is diagnosed with, or suspected of having an infection;
  measuring or determining the level of one or more cytokines or inflammatory biomarkers in a sample of the individual;
  if the level of the one or more cytokines or inflammatory biomarkers in the sample is higher than the level in a reference data set in the form of data representative of one or more individuals who do not have early stage organ damage caused by inflammation associated with infection, then administering a therapeutically effective amount of idronoxil, or derivative, pharmaceutically acceptable salt, ester, amide, polymorph and/or prodrug thereof to the individual;
  thereby treating the individual with idronoxil, or derivative, pharmaceutically acceptable salt, ester, amide, polymorph and/or prodrug thereof.

In another aspect, the present invention provides a method of treating an individual with idronoxil, or derivative, pharmaceutically acceptable salt, ester, amide, polymorph and/or prodrug thereof, the method comprising, consisting essentially of, or consisting of the steps of:
  providing an individual who is diagnosed with, or suspected of having an infection;
  measuring or determining the level of one or more cytokines or inflammatory biomarkers in a sample of the individual;
  if the level of the one or more cytokines or inflammatory biomarkers in the sample is the same or higher than the level in a reference data set in the form of data representative of one or more individuals who have early stage organ damage caused by inflammation associated with infection, then administering a therapeutically effective amount of idronoxil, or derivative, pharmaceutically acceptable salt, ester, amide, polymorph and/or prodrug thereof to the individual;
  thereby treating the individual with idronoxil, or derivative, pharmaceutically acceptable salt, ester, amide, polymorph and/or prodrug thereof.

In another aspect, the present invention also provides use of idronoxil, or derivative, pharmaceutically acceptable salt, ester, amide, polymorph and/or prodrug thereof in the manufacture of a medicament for:
  treating inflammation in an individual, wherein the individual is diagnosed with or suspected of having early stage organ damage caused by inflammation associated with infection;
  treating inflammation in an individual, wherein the individual is diagnosed with or suspected of having inflammation characterised as prior to late stage organ damage caused by inflammation associated with infection;
  treatment or reduction of the severity of a symptom of early stage organ damage caused by inflammation associated with infection in an individual;
  alleviating or ameliorating a symptom of early stage organ damage caused by inflammation associated with infection in an individual;
  inhibiting or minimising the progression of a symptom of early stage organ damage caused by inflammation associated with infection in an individual; and/or
  preventing or reducing the severity of sepsis caused by inflammation associated with infection in an individual.

In another aspect, the present invention also provides idronoxil, or derivative, pharmaceutically acceptable salt, ester, amide, polymorph and/or prodrug thereof for use in:
  treating inflammation in an individual, wherein the individual is diagnosed with or suspected of having early stage organ damage caused by inflammation associated with infection;
  treating inflammation in an individual, wherein the individual is diagnosed with or suspected of having inflammation characterised as prior to late stage organ damage caused by inflammation associated with infection;
  treatment or reduction of the severity of a symptom of early stage organ damage caused by inflammation associated with infection in an individual;
  alleviating or ameliorating a symptom of early stage organ damage caused by inflammation associated with infection in an individual;
  inhibiting or minimising the progression of a symptom of early stage organ damage caused by inflammation associated with infection in an individual; and/or
  preventing or reducing the severity of sepsis caused by inflammation associated with infection in an individual.

In another aspect, the present invention also provides a pharmaceutical composition comprising, consisting essentially of, or consisting of idronoxil, or derivative, pharmaceutically acceptable salt, ester, amide, polymorph and/or prodrug thereof, and a pharmaceutically acceptable carrier, diluent or excipient for use in:

treating inflammation in an individual, wherein the individual is diagnosed with or suspected of having early stage organ damage caused by inflammation associated with infection;

treating inflammation in an individual, wherein the individual is diagnosed with or suspected of having inflammation characterised as prior to late stage organ damage caused by inflammation associated with infection;

treatment or reduction of the severity of a symptom of early stage organ damage caused by inflammation associated with infection in an individual;

alleviating or ameliorating a symptom of early stage organ damage caused by inflammation associated with infection in an individual;

inhibiting or minimising the progression of a symptom of early stage organ damage caused by inflammation associated with infection in an individual; and/or preventing or reducing the severity of sepsis caused by inflammation associated with infection in an individual.

In one aspect, preferably the only active ingredient present in the composition is idronoxil, or derivative, pharmaceutically acceptable salt, ester, amide, polymorph and/or prodrug thereof.

In another aspect, the invention provides a pharmaceutical composition for treating inflammation in an individual, wherein the individual is diagnosed with or suspected of having early stage organ damage caused by inflammation associated with infection, comprising as an active ingredient idronoxil, or derivative, pharmaceutically acceptable salt, ester, amide, polymorph and/or prodrug thereof, and a pharmaceutically acceptable diluent, excipient or carrier. In one embodiment, the only active ingredient present in the composition is idronoxil, or derivative, pharmaceutically acceptable salt, ester, amide, polymorph and/or prodrug thereof.

In another aspect, the invention provides a pharmaceutical composition for treating inflammation in an individual, wherein the individual is diagnosed with or suspected of having early stage organ damage caused by inflammation associated with infection, comprising as a main ingredient idronoxil, or derivative, pharmaceutically acceptable salt, ester, amide, polymorph and/or prodrug thereof, and a pharmaceutically acceptable diluent, excipient or carrier. In one embodiment, the only active ingredient present in the composition is idronoxil, or derivative, pharmaceutically acceptable salt, ester, amide, polymorph and/or prodrug thereof.

In another aspect, the invention provides a pharmaceutical composition for treating inflammation in an individual, wherein the individual is diagnosed with or suspected of having inflammation characterised as prior to late stage organ damage caused by inflammation, wherein the inflammation is associated with infection, comprising as an active ingredient idronoxil, or derivative, pharmaceutically acceptable salt, ester, amide, polymorph and/or prodrug thereof, and a pharmaceutically acceptable diluent, excipient or carrier. In one embodiment, the only active ingredient present in the composition is idronoxil, or derivative, pharmaceutically acceptable salt, ester, amide, polymorph and/or prodrug thereof.

In another aspect, the invention provides a pharmaceutical composition for treating inflammation in an individual, wherein the individual is diagnosed with or suspected of having inflammation characterised as prior to late stage organ damage caused by inflammation, wherein the inflammation is associated with infection, comprising as a main ingredient idronoxil, or derivative, pharmaceutically acceptable salt, ester, amide, polymorph and/or prodrug thereof, and a pharmaceutically acceptable diluent, excipient or carrier. In one embodiment, the only active ingredient present in the composition is idronoxil, or derivative, pharmaceutically acceptable salt, ester, amide, polymorph and/or prodrug thereof.

In any method, use or composition of the invention described above, the idronoxil, or derivative, pharmaceutically acceptable salt, ester, amide, polymorph and/or prodrug thereof, may be administered in combination with one or more active substances, optionally including intravenous fluids. Preferably, the active substance is selected from: antibiotics, corticosteroids, such as glucocorticoids, mineralocorticoids and combinations thereof. More preferably, the active substance is an antibiotic. The administration of idronoxil, or derivative, pharmaceutically acceptable salt, ester, amide, polymorph and/or prodrug thereof, and active substance, optionally including intravenous fluids, may include simultaneous, sequential and/or separate (immediate or prolonged delays between) administration. Sequential and/or separate administration may be in any order. For example, the idronoxil, or derivative, pharmaceutically acceptable salt, ester, amide, polymorph and/or prodrug thereof, may be administered prior to or after administration of the active substance, optionally including intravenous fluids, to the individual.

In any aspect of the present invention, preferably the infection is caused by bacteria, viruses, fungi or protozoa.

In one preferred embodiment, the infection is caused by a virus. The virus is preferably selected from: coronavirus, influenza, parainfluenza, respiratory syncytial virus (RSV), adenovirus, cytomegalovirus (CMV), Epstein-Barr virus (EBV), varicella zoster virus (VZV), dengue virus, rhinovirus, Herpes simplex virus and enteroviruses. More preferably, the virus is coronavirus or influenza. Even more preferably, the virus is severe acute respiratory syndrome coronavirus (SARS-CoV), Middle East respiratory syndrome coronavirus (MERS-CoV), or severe acute respiratory syndrome coronavirus 2 (SARS-CoV-2), most preferably SARS-CoV-2.

In an alternative preferred embodiment, the infection is caused by bacteria. The bacteria are preferably selected from: Streptococcus spp., *Escherichia coli, Pseudomonas aeruginosa, Haemophilus influenza, Klebsiella pneumoniae*, and *Acinetobacter baumannii* and *Neisseria meningitidis*. Streptococcus spp. includes, but is not limited to, *Staphylococcus aureus, Streptococcus pyogenes*, and *Streptococcus pneumoniae*. In one embodiment, wherein the sepsis is caused by bacteria, the individual is diagnosed with or suspected of having a viral infection. Preferably the viral infection is caused by a virus selected from: coronavirus, influenza, parainfluenza, respiratory syncytial virus (RSV), adenovirus, cytomegalovirus (CMV), Epstein-Barr virus (EBV), varicella zoster virus (VZV), dengue virus, rhinovirus, Herpes simplex virus and enteroviruses. More preferably, the viral infection is caused by coronavirus or influenza. Even more preferably, the viral infection is caused by severe acute respiratory syndrome coronavirus (SARS-CoV), Middle East respiratory syndrome coronavirus (MERS-CoV), and severe acute respiratory syndrome coronavirus 2 (SARS-CoV-2), most preferably SARS-CoV-2

In any aspect of the present invention, preferably the individual has not been administered idronoxil, or derivative, pharmaceutically acceptable salt, ester, amide, polymorph and/or prodrug thereof at the onset of infection. In any aspect of the present invention, preferably the individual has not been administered idronoxil, or derivative, pharmaceutically acceptable salt, ester, amide, polymorph and/or prodrug thereof at the onset of inflammation. Preferably, administration consists essentially of, or consists of the period from early stage organ damage to prior to late stage organ damage caused by inflammation.

In any method or use of the invention described herein, idronoxil, or derivative, pharmaceutically acceptable salt, ester, amide, polymorph and/or prodrug thereof may be administered systemically or directly to the site of disease. Idronoxil, or derivative, pharmaceutically acceptable salt, ester, amide, polymorph and/or prodrug thereof may be formulated for oral administration. In certain embodiments, idronoxil, or derivative, pharmaceutically acceptable salt, ester, amide, polymorph and/or prodrug thereof may be formulated for nasal, intravenous or rectal administration.

In another aspect, the present invention also provides a kit for use, or when used, in a method of the invention, the kit comprising, consisting essentially of or consisting of:
 idronoxil or derivative, pharmaceutically acceptable salt, ester, amide, polymorph and/or prodrug thereof as described herein; and optionally
 written instructions describing the use of idronoxil or derivative, pharmaceutically acceptable salt, ester, amide, polymorph and/or prodrug thereof in a method of the invention.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

Figure 4:
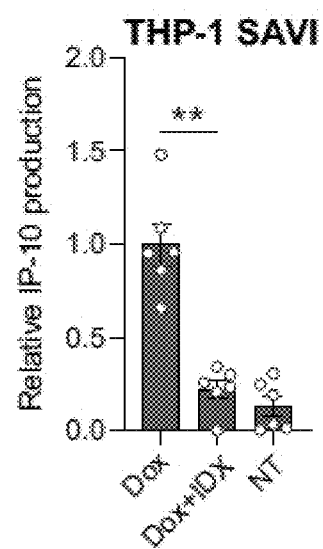
FIG. 4: Human THP-1 cells expressing a Doxycycline-inducible variant of human STING R284S mutant (activating mutation), were pre-treated with 2.5 uM IDX for 1 h prior overnight stimulation with Dox (inducing STING expression and signalling). IP-10 levels were measured in supernatants the next day by ELISA. Data shown are averaged from two independent experiments in biological triplicate, reported to the Dox only condition (t SEM).
Figure 5:
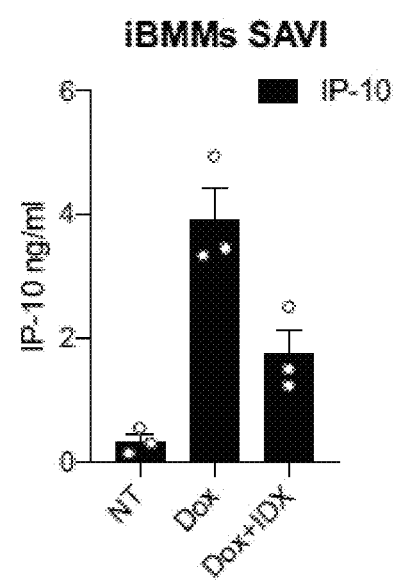
FIG. 5: Mouse immortalised bone macrophages (iBMMs) stably expressing the Dox-inducible R284S STING mutant were treated for 1 h with 2.5 uM IDX prior to Dox stimulation overnight. IP-10 levels were measured by ELISA the next day. Data shown are from a single experiment in biological triplicate (±SEM).

NT: Non-treated. Each biological data point is shown in FIGS. 4 and 5. IDX was not removed during stimulation phase by DMXAA or TLR ligands.

Figure 7:
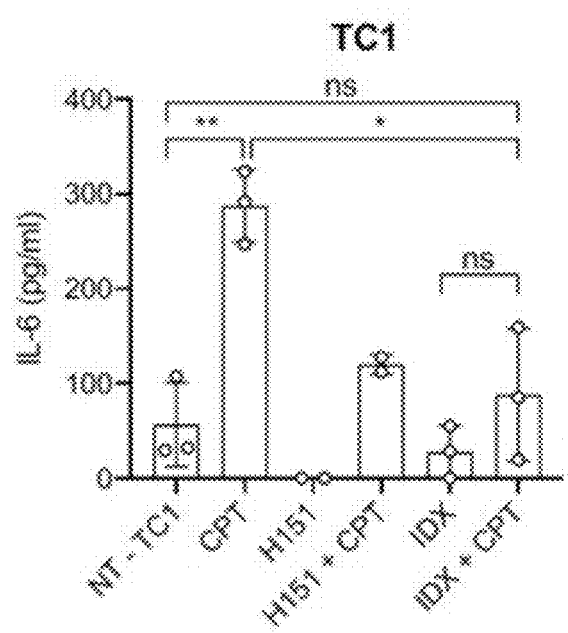

FIG. 7: Mouse TC-1 cells were plated in the presence of 0.5 μM CPT for 48 hours, with the following compounds, where indicated: H151 (1.8 μM), IDX (2.5 μM). IL-6 levels were determined by ELISA. Data shown are averaged from 2 (for H151) or 3 independent experiments (conducted with biological replicate), ±standard deviation (SD). Unpaired two-tailed t-tests comparing indicated conditions are shown. Each point represents the mean data for each independent experiment; the column represents the mean of the experiments. *, $P \leq 0.05$; , $P \leq 0.01$; *, $P \leq 0.001$; ****, $P \leq 0.0001$, ns: non-significant.

Figure 8:
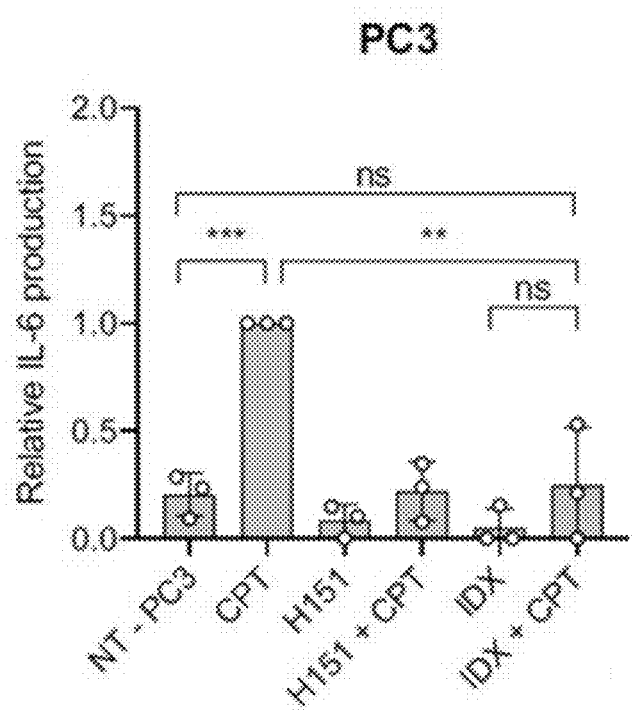

FIG. 8: Human PC-3 cells were plated in the presence of 0.5 μM CPT for 20 hours, with the following compounds, where indicated: H151 (1.8 μM), IDX (1.25 μM).

IL-6 levels were determined by ELISA. Data were normalised to the CPT only condition and are shown as averages from 3 independent experiments (conducted with biological replicate), ±SD. Unpaired two-tailed t-tests comparing indicated conditions are shown. Each point represents the mean data for each independent experiment; the column represents the mean of the experiments. *, $P \leq 0.05$; , $P \leq 0.01$; *, $P \leq 0.001$; *, $P \leq 0.0001$, ns: non-significant.

Figure 9:
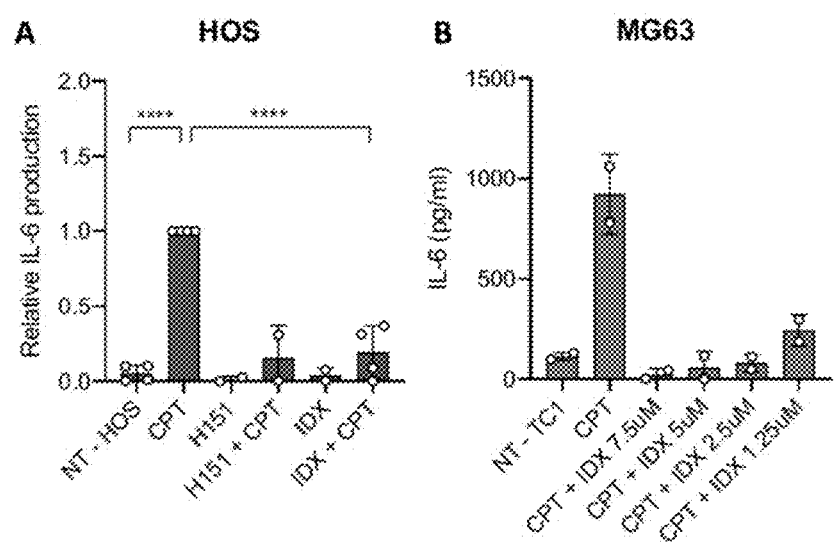

FIG. 9: A. Human HOS cells were plated in the presence of 0.2 μM CPT for 48 hours, with the following compounds, where indicated: H151 (1.8 μM), IDX (1.25 μM). IL-6 levels were determined by ELISA. Data were normalised to the CPT only condition and are shown as averages from 2 (H151 and IDX only conditions) or 4 independent experiments (conducted with biological replicate), ±SD. Unpaired two-tailed t-tests comparing indicated conditions are shown. B. Human MG63 cells were plated in the presence of 0.1 μM CPT for 48 hours, with indicated doses of IDX (7.5, 5, 2.5 and 1.25 μM). IL-6 levels were determined by ELISA. Data shown are averaged from 2 independent experiments (conducted with biological replicate), ±SD. Each point represents the mean data for each independent experiment; the column represents the mean of the experiments. *, $P \leq 0.05$; , $P \leq 0.01$; *, $P \leq 0.001$; ****, $P \leq 0.0001$, ns: non-significant.

Figure 10:
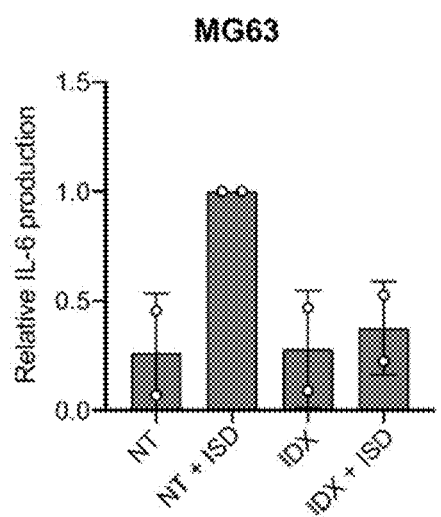

FIG. 10: MG63 cells were pre-treated with 1.25 μM IDX for 40 hours, prior to being plated and transfected with 2.5 μg/mL of ISD with lipofectamine 2000. IP-10 levels were measured by ELISA after overnight incubation with ISD. Data were normalised to the ISD only condition, and are shown as averages from 2 independent experiments (conducted with biological replicate), ±SD. Each point represents the mean data for each independent experiment; the column represents the mean of the experiments.

Figure 11:
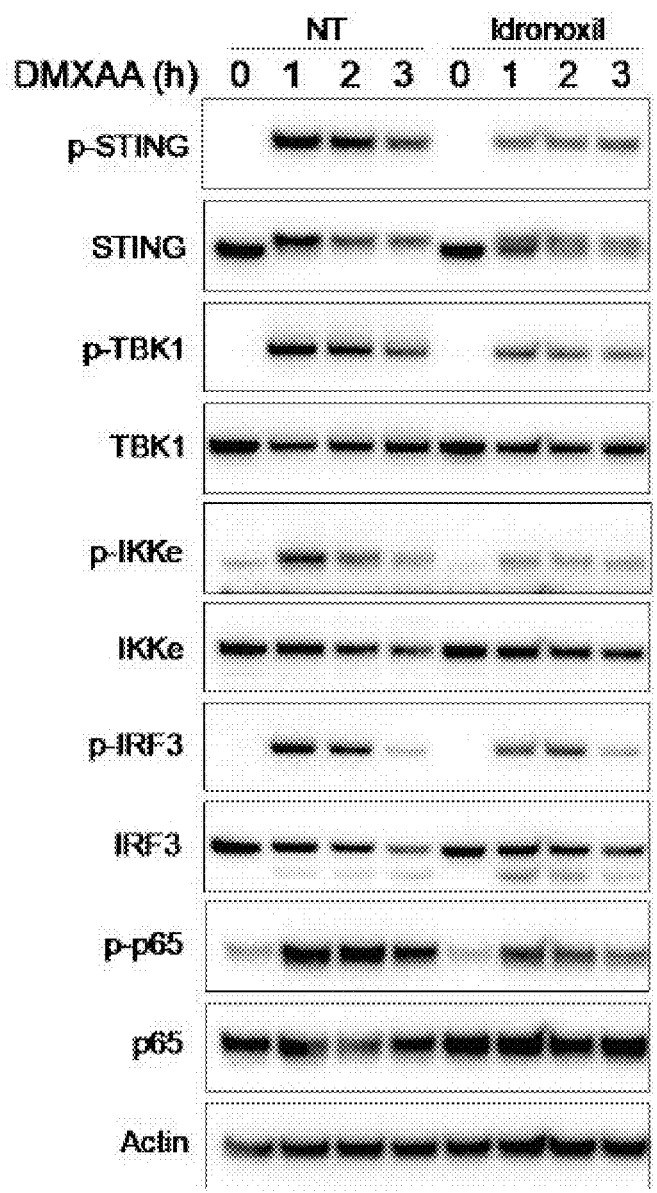

FIG. 11: Immortalised mouse bone marrow derived macrophages were pre-treated for 1 hour with 2.5 uM IDX prior to stimulation for an indicated amount of time with DMXAA (50 ug/mL), and then lysed and analysed by Western blotting using specific total or phospho-antibody. The results on STING and p-STING are representative of 3 independent experiments.

Figure 12:
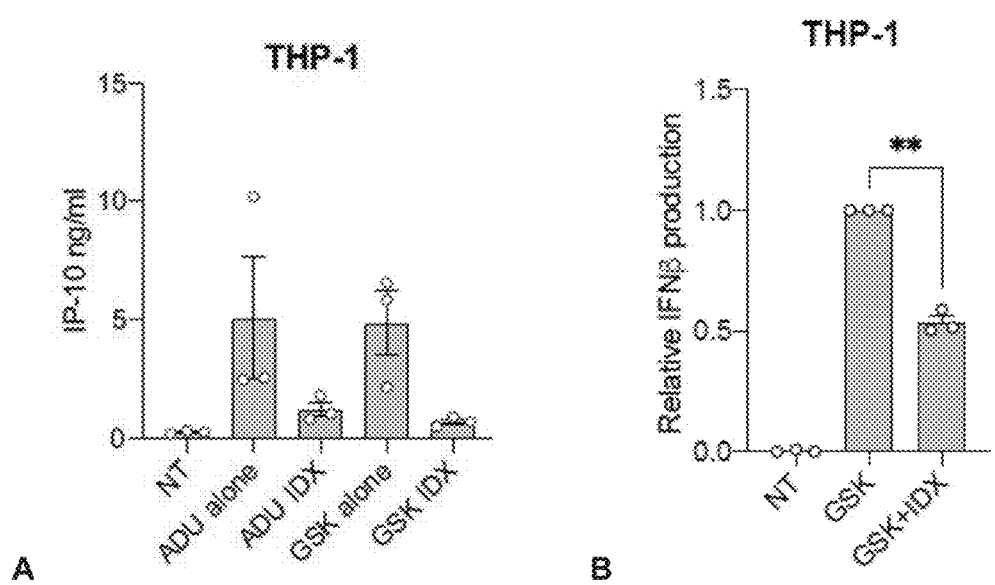

FIG. 12: Human THP-1 cells were pre-treated for 1 hour with 2.5 uM IDX prior to being stimulated with human STING agonist for 6 hours (cGAMP synthetic analogue ADU-S100 at 30 uM or GSK synthetic STING agonist at 100 nM—(1)). The supernatants were collected and analysed for IP-10 production by ELISA (left panel), or IFNβ ELISA (right panel). Data shown are an average from 3 independent experiments (conducted with biological replicate), ±SEM (left panel), or normalised to the GSK condition (right panel), ±SEM (unpaired t-test with Welch's correction shown). **, $P \leq 0.01$.

Figure 13:
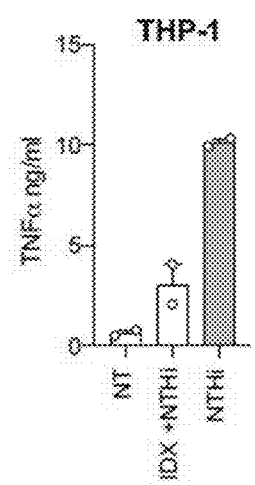

FIG. 13: PMA-differentiated THP-1 cells were pre-treated with 2.5 uM IDX for 1 hour, prior to infection with non-typeable *Haemophilus influenzae* (NTHi) (100 CFU/cell) for 3 hours in the absence of serum or antibiotics. The cells were washed twice with penicillin/streptomycin containing medium to remove and kill extracellular bacteria and incubated overnight at 37° C. TNF-α ELISA was performed on supernatants after overnight incubation. Data shown are an average from two independent experiments (conducted in biological replicate).

Figure 14:
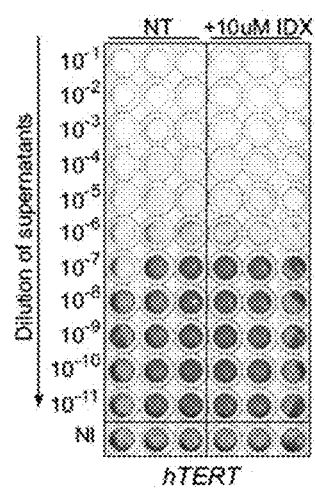

FIG. 14: Human hTERT immortalised foreskin fibroblasts were pre-treated for 72 hours with 10 uM IDX, prior to being plated infected with Semliki Forest virus (SFV-MOI of 2) for 24 hours. Supernatants containing infectious viral particles were subsequently tittered by 10-fold serial dilution on confluent Vero cells for 48 hours as previously reported (2).

Figure 15:
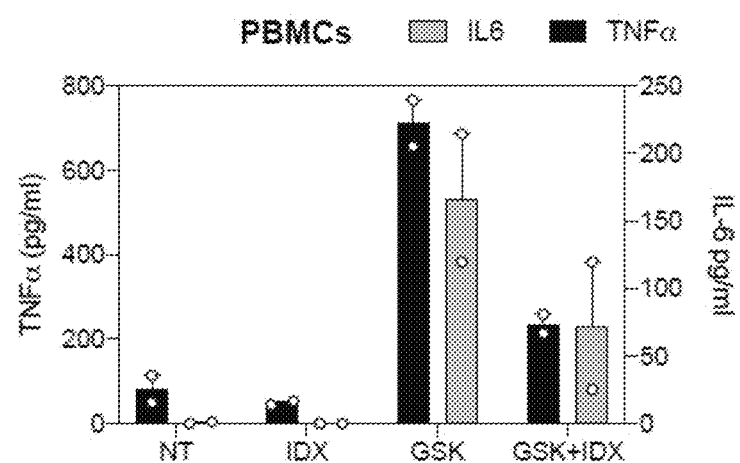

FIG. 15: Human PBMCs from two different blood donors were stimulated for 1 h with 2.5 uM IDX, prior to stimulation with the human STING agonist for 6 hours (GSK synthetic STING agonist at 100 nM). The supernatants were collected and analysed for IL-6 and TNFα production by ELISA. Data shown are as average from 2 independent donors (conducted with biological replicate for each donor), ±SEM.

Figure 16:
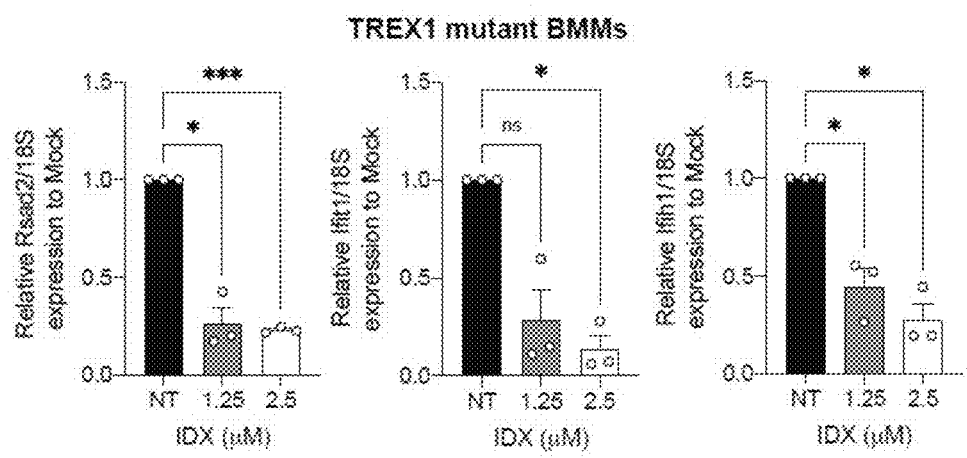

FIG. 16: Primary bone marrow derived macrophages from Trex1-mutant mice were treated overnight with IDX at indicated doses, prior to RNA collection and RT-qPCR analysis. Expression of the indicated interferon stimulated genes was measured relative to that of the housekeeping 18S RNA, and normalised to the non-treated condition. Data shown are averaged from 3 independent mice bone marrow (conducted with biological replicate for each mice), ±SEM. One-way ANOVA with Dunnett's multiple comparisons to NT condition are shown. *, $P \leq 0.05$; ***, $P \leq 0.001$; ns: non-significant.

Figure 17:
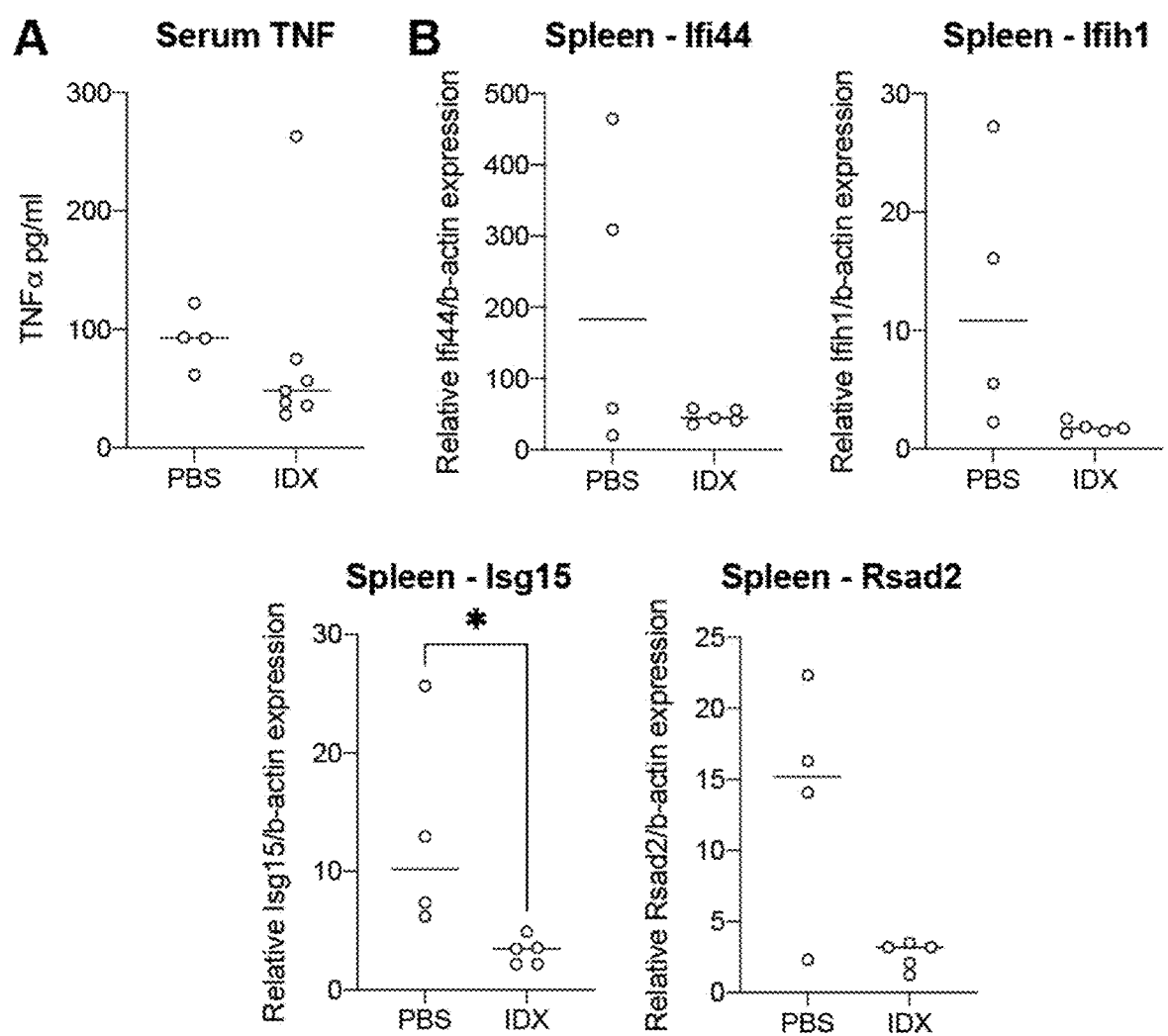

FIG. 17: 7 week-old Trex1-mutant mice were injected i.p. for 10 consecutive days with 2 mg/kg IDX solution in PBS, prior to serum and spleen collection. Sera were analysed for TNFα by LEGENDplex bead-based immunoassay, while RNA purified from the spleens was analysed by RT-qPCR (for Ifi44/Isg15/Ifih1/Rsad2 reported to b-Actin expression). Each point represents one mouse (noting that RNA was only collected for 5 Trex1 IDX treated mice, but sera was collected from 7 mice of this cohort). The median expression of each cohort is shown with a line. Unpaired Mann Whitney U-test is shown *, $P \leq 0.05$.

Figure 18:
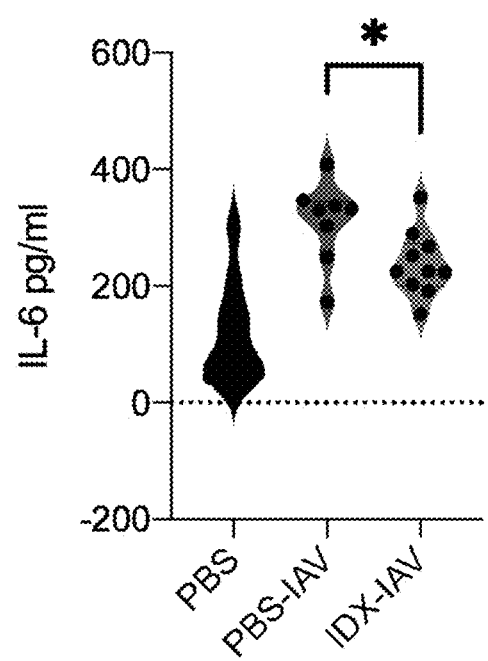

FIG. 18: 8-10 week old transgenic mice that selectively over-expresses active TGF-β1 in the lung following doxycycline (Dox) administration were infected with IAV (or not) after 48 h Dox administration. Starting the next day, the mice were injected with PBS or PBS/IDX solution (5 mg/kg), until day three post-infection. Bronchial Alveolar Lavages were collected and IL-6 levels analysed by ELISA. Each dot on the graph represents a mouse. Violin plots show the overall population variation, and unpaired two tail t-test is shown *, $P \leq 0.05$.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

As used herein, "preventing" or "prevention" is intended to refer to at least the reduction of likelihood of the risk of (or susceptibility to) acquiring a disease or disorder (i.e., causing at least one of the clinical symptoms of the disease not to develop in an individual that may be exposed to or predisposed to the disease but does not yet experience or display symptoms of the disease). Biological and physiological parameters for identifying such patients are provided herein and are also well known by physicians.

In particularly preferred embodiments, the methods of the present invention can be to prevent or reduce the severity, or inhibit or minimise progression, of a symptom of a disease or condition as described herein. As such, the methods of the present invention have utility as treatments as well as prophylaxes.

The terms "treatment" or "treating" of a subject includes delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the individual; slowing in the rate of degeneration or decline; making the final point of degeneration less debilitating.

A "subject" herein is preferably a human subject. It will be understood that the terms "subject" and "individual" are interchangeable in relation to an individual requiring treatment according to the present invention.

The work of the inventors leading to the invention includes the unexpected finding that idronoxil inhibits the STING pathway. STING is a key element of the innate immune system. The cGAS/STING pathway is responsible for sensing cytosolic DNA. This cytosolic DNA can originate from pathogens causing an infection, or from cellular DNA leaked from the nucleus or the mitochondria (as seen in acute kidney injury, or response to DNA damage). Damaged tissue is also thought to release DNA which triggers STING in phagocytes (for e.g. in myocardial infarction, acute pancreatitis, lung silicosis, radiation induced liver injury). Activation of the cGAS/STING pathway leads to the rapid stimulation of a potent inflammatory response. This response is characterised by strong induction of type I interferons and pro-inflammatory cytokines such as IL-6, TNF-α and IFN-beta. Clinically the inflammatory response is characterized by increased blood flow, increased capillary permeability, and the influx of phagocytic cells.

Upon binding cytosolic DNA, the protein cyclic GMP-AMP Synthase (cGAS) triggers reaction of GTP and ATP to form cyclic GMP-AMP (cGAMP). cGAMP binds to Stimulator of Interferon Genes (STING) which triggers phosphorylation of IRF3 and NF-kB via TBK1/IKKε. IRF3 and NF-kB then triggers transcription of inflammatory genes.

At the onset of infection, activation of the inflammatory pathway via NF-kB provides a protective immune effect. NF-kB regulates the immune response to infection by recruiting white blood cells which produce cytokines.

Administration of inhibitors of NF-kB at the onset of infection, and inhibitors of downstream targets of NF-kB, including cytokines, may adversely impact the innate immune response to the infection as seen with the inhibition of the inflammasome during early influenza infection (1). Similarly, inhibition of the STING pathway early in infections may prevent production of antiviral factors such as type I interferons (2).

In some circumstances, the inflammatory response develops into a hyper-acute inflammatory response known as a cytokine response syndrome associated with an abnormally excessive immune response and resulting in hyperacute inflammation. In such circumstances, where the inflammation associated with infection does not resolve, inhibitors of alternative inflammatory pathways, such as STING, which also controls the IRF3 pathway, are expected to resolve inflammation and infection where inhibitors of NF-kB alone would not.

Idronoxil may therefore be used in accordance with aspects of the invention described herein to treat inflammation associated with infection, wherein the individual is identified as having, or suspected of having early stage organ damage caused by the inflammation. Treatment at the onset of early stage organ damage targets individuals who do not have the adequate immune response to fight the infection.

The invention therefore finds application in the treatment of inflammation in an individual comprising, consisting essentially of or consisting of the steps of:

administering a therapeutically effective amount of idronoxil, or derivative, pharmaceutically acceptable salt, ester, amide, polymorph and/or prodrug thereof to the individual;

wherein the individual is diagnosed with, or suspected of having, early stage organ damage caused by inflammation associated with infection, thereby treating the inflammation.

In another aspect, the present invention provides a method of treating inflammation in an individual comprising, consisting essentially of or consisting of the steps of:

administering a therapeutically effective amount of idronoxil, or derivative, pharmaceutically acceptable salt, ester, amide, polymorph and/or prodrug thereof to the individual;

wherein administration is prior to late stage organ damage caused by inflammation associated with infection, thereby treating the inflammation.

In certain embodiments, the methods, uses or compositions of the invention find utility in treating or minimising the severity of a symptom of early stage organ damage caused by inflammation associated with infection.

In certain embodiments, the methods, uses or compositions of the invention find utility in inhibiting or minimising the progression of a symptom of early stage organ damage caused by inflammation associated with infection.

In other embodiments, the methods, uses or compositions of the invention find utility in preventing or reducing the severity of sepsis caused by inflammation associated with infection.

Preferably the individual has not been administered idronoxil, or derivative, pharmaceutically acceptable salt, ester, amide, polymorph and/or prodrug thereof at the onset of infection.

Preferably the individual has not been administered idronoxil, or derivative, pharmaceutically acceptable salt, ester, amide, polymorph and/or prodrug thereof at the onset of inflammation.

Preferably, administration consists essentially of, or consists of the period from early stage organ damage to prior to late stage organ damage caused by inflammation and/or sepsis.

The onset of infection and inflammation may be characterised by elevated body temperature, preferably greater than 38° C. Preferably, wherein the infection is caused by SARS-CoV-2, the onset of infection and inflammation is also characterised by a dry cough.

Early stage organ damage as used herein refers to the period after the onset of infection and inflammation, and prior to late stage organ damage caused by inflammation and/or sepsis. The inflammation during early stage organ damage is hyperacute inflammation.

Symptoms of early stage organ damage include but are not limited to: abnormal levels of one or more cytokines or inflammatory biomarkers, abnormal levels of clotting factors, abnormal levels of troponin I, abnormal levels of alanine aminotransferase, abnormal levels of blood urea nitrogen, abnormal levels of creatinine, abnormal levels of procalcitonin, abnormal levels of lactic dehydrogenase, elevated body temperature, elevated heart rate, elevated respiratory rate, abnormal lymphocyte cell count, abnormal neutrophil cell count, abnormal platelet cell count, low blood pressure, hypoxemia, tissue hypoxia, hypoperfusion, redness and swelling around a wound, low urine volume, dizziness or faintness, pale, discoloured or mottled skin, slurred speech, rigors, malaise, fatigue, anorexia, myalgia, arthralgia, nausea, vomiting, headache, rash, vomiting, diarrhoea, widened pulse pressure, increased cardiac output (early), potentially diminished cardiac output (late), hypofibrinogenemia ±bleeding, azotemia, transaminitis, hyperbilirubinemia, mental status changes, confusion, delirium, word finding difficulty or frank aphasia, hallucinations, tremor, dysmetria, altered gait, seizures and combinations thereof. Preferably, the individual is identified as having, or suspected of having, at least 2, 3, 4, 5, or 6 symptoms of early stage organ damage.

The one or more cytokines or inflammatory biomarkers may be selected from: interleukin-1 (IL-1), interleukin-6 (IL-6), interleukin-8 (IL-8), interleukin-11 (IL-11), interleukin-12 (IL-12), interleukin-17 (IL-17), interleukin-18 (IL-18), interleukin-37 (IL-37), IP-10, tumour necrosis factor-alpha (TNF-α), interferon-gamma (IFN-γ), granulocyte-macrophage colony stimulating factor (GM-CSF), transforming growth factor-beta (TGF-β), interleukin-2 receptor (IL-2R), interleukin-4 (IL-4), interleukin-10 (IL-10), interleukin-13 (IL-13), interferon-alpha (IFN-α), interferon-beta (IFN-β), monocyte chemoattractant protein-1 (MCP-1 or CCL2), procalcitonin (PCT), C-reactive protein (CRP), C-C Motif Chemokine Ligand 5 (CCL5 or RANTES), β-2-microglobulin (β-2M), serum ferritin, D-dimer, cyclic guanosine monophosphate-adenosine monophosphate (cGAMP), and combinations thereof. More preferably, the one or more cytokines or inflammatory biomarkers may be selected from: IL-1β, IL-2R, IL-6, IL-8, IL-10, IL-12, IP-10, TNF-α, MCP-1, PCT, CRP, β-2M, serum ferritin, D-dimer, cGAMP, CCL5 (RANTES), IFN-α, IFN-β, IFN-γ and combinations thereof. Even more preferably, the one or more cytokines or inflammatory biomarkers may be selected from: IL-6, IP-10, PCT, CRP, D-dimer, and combinations thereof. Preferably, the individual is identified as having abnormal levels of at least 2, 3, 4, 5, or 6 cytokines or inflammatory biomarkers.

Symptoms of early stage organ damage identified by biochemical or clinical tests known to those skilled in the art may include, but are not limited to:
  temperature greater than about 38° C.,
  heart rate greater than about 90 beats/min,
  respiratory rate greater than about 20 breaths/min and/or arterial $pCO_2$ less than 32 mmHg,
  white blood cell count below about $10.0 \times 10^9$/L,
  lymphocyte cell count below about $2.0 \times 10^9$/L, preferably between about $0.9$-$1.6 \times 10^9$/L,
  procalcitonin (PCT) level below about 0.1 ng/mL, preferably between about 0.05 and about 0.1 ng/mL,
  D-dimer level greater than about 1 ug/mL, preferably between about 1-2.5 ug/mL,
  C reactive protein level greater than 3 mg/L, preferably between about 3-25 mg/L
  IL-2R level greater than about 333 U/mL, preferably between about 333 and about 630 U/mL,
  IL-6 level greater than about 1.7 pg/mL, preferably between about 1.7 pg/mL and about 15 pg/mL,
  IL-8 level greater than about 9 pg/mL, preferably between about 9 pg/mL and about 30 pg/mL,
  IL-10 level greater than about 3 pg/mL, preferably between about 3 pg/mL and about 5 pg/mL,
  TNF level greater than about 3 pg/mL, preferably between about 3 pg/mL and about 9.5 pg/mL,
  Beta 2 Microbulin (B2M) level greater than 3 ug/mL,
  Arterial oxygen tension ($Pao_2$) less than 80 mmHg, and/or
  elevated levels of one or more of: IL-1β, lactate, and HMGB1.

In some embodiments, the use of idronoxil, or derivative, pharmaceutically acceptable salt, ester, amide, polymorph and/or prodrug thereof, in accordance with the methods of the present invention, affects a proinflammatory cytokine, for instance by facilitating or effectuating a decrease or reduction in a quantity of pro-inflammatory cytokines or pro-inflammatory mediators in blood, serum, plasma, bronchoalveolar lavage fluid, urine, and/or saliva of the individual having, or suspected of having, early organ damage caused by inflammation associated with infection.

Examples of pro-inflammatory cytokines or pro-inflammatory mediators include interleukin-1 (IL-1), interleukin-6 (IL-6), interleukin-8 (IL-8), interleukin-11 (IL-11), interleukin-12 (IL-12), interleukin-17 (IL-17), interleukin-18 (IL-18), tumour necrosis factor-alpha (TNF-α), interferon-gamma (IFN-γ), granulocyte-macrophage colony stimulating factor (GM-CSF), transforming growth factor-beta (TGF-β), CCL2 (MCP-1), and CCL5 (RANTES). It will be appreciated by the skilled person that references to pro-inflammatory cytokines in most embodiments of the present disclosure can refer to any one or more of pro-inflammatory cytokines known in the art, and including one or more of the above-listed examples of pro-inflammatory cytokines.

In some embodiments, the decrease in quantity of pro-inflammatory cytokines within the individual assists in preventing, controlling, down-regulating, and/or stopping the occurrence of late stage organ damage and/or sepsis in the individual.

The skilled person can identify or diagnose early stage organ damage caused by inflammation associated with infection in an individual by measuring levels of one or more suitable cytokines or inflammatory biomarkers in a sample of the individual, for example 1, 2, 3, 4, 5, 6, 7, 8, 9, 10 or more cytokines or inflammatory biomarkers can be measured, such as cytokines or inflammatory biomarkers independently selected from: interleukin-1 (IL-1), interleukin-6 (IL-6), interleukin-8 (IL-8), interleukin-11 (IL-11), interleukin-12 (IL-12), interleukin-17 (IL-17), interleukin-18 (IL-18), interleukin-37 (IL-37), IP-10, tumour necrosis factor-alpha (TNF-α), interferon-gamma (IFN-γ), granulocyte-macrophage colony stimulating factor (GM-CSF), transforming growth factor-beta (TGF-β), interleukin-2 receptor (IL-2R), interleukin-4 (IL-4), interleukin-10 (IL-10), interleukin-13 (IL-13), interferon-alpha (IFN-α), interferon-beta (IFN-β), monocyte chemoattractant protein-1 (MCP-1 or CCL2), procalcitonin (PCT), C-reactive protein (CRP), C-C Motif Chemokine Ligand 5 (CCL5 or RANTES), β-2-microglobulin (β-2M), serum ferritin, D-dimer, cyclic guanosine monophosphate-adenosine monophosphate (cGAMP), and combinations thereof. More preferably, the one or more cytokines or inflammatory biomarkers may be selected from: IL-1β, IL-2R, IL-6, IL-8, IL-10, IL-12, IP-10, TNF-α, MCP-1, PCT, CRP, β-2M, serum ferritin, D-dimer, cGAMP, CCL5 (RANTES), IFN-α, IFN-β, IFN-γ and combinations thereof. Even more preferably, the one or more cytokines or inflammatory biomarkers may be selected from: IL-6, IP-10, PCT, CRP, D-dimer, and combinations thereof.

Accordingly, in still another aspect the present invention provides a method of treating an individual with idronoxil, or derivative, pharmaceutically acceptable salt, ester, amide, polymorph and/or prodrug thereof, the method comprising, consisting essentially of, or consisting of the steps of:
  providing an individual who is diagnosed with, or suspected of having an infection;
  measuring or determining the level of one or more cytokines or inflammatory biomarkers in a sample of the individual;
  if the level of the one or more cytokines or inflammatory biomarkers in the sample is higher than the level in a reference data set in the form of data representative of one or more individuals who do not have early stage organ damage caused by inflammation associated with infection, then administering a therapeutically effective amount of idronoxil, or derivative, pharmaceutically acceptable salt, ester, amide, polymorph and/or prodrug thereof to the individual;

thereby treating the individual with idronoxil, or derivative, pharmaceutically acceptable salt, ester, amide, polymorph and/or prodrug thereof.

In another aspect, the present invention provides a method of treating an individual with idronoxil, or derivative, pharmaceutically acceptable salt, ester, amide, polymorph and/or prodrug thereof, the method comprising, consisting essentially of, or consisting of the steps of:

providing an individual who is diagnosed with, or suspected of having an infection;

measuring or determining the level of one or more cytokines or inflammatory biomarkers in a sample of the individual;

if the level of the one or more cytokines or inflammatory biomarkers in the sample is the same or higher than the level in a reference data set in the form of data representative of one or more individuals who have early stage organ damage caused by inflammation associated with infection, then administering a therapeutically effective amount of idronoxil, or derivative, pharmaceutically acceptable salt, ester, amide, polymorph and/or prodrug thereof to the individual;

thereby treating the individual with idronoxil, or derivative, pharmaceutically acceptable salt, ester, amide, polymorph and/or prodrug thereof.

The sample is a biological sample from the individual, preferably a bodily fluid sample, including but not limited to: blood, serum, plasma, bronchoalveolar lavage fluid, urine, and/or saliva sample. Preferably, the sample is a serum sample.

In performing the methods of the present invention, a determination is made by reference to the level of one or more cytokines or inflammatory biomarkers in the sample of an individual in a relevant control profile or reference data set comprising a plurality of control profiles. The reference data set may be in the form of representative data from one or more healthy individuals, more particularly, individuals who do not have early stage organ damage caused by inflammation associated with infection. Alternatively the reference data set may be in the form of representative data from one or more individuals identified or diagnosed as having early stage organ damage caused by inflammation associated with infection.

It will be appreciated that the control profile for diagnosing or determining likelihood of the individual having early stage organ damage caused by inflammation associated with infection, may be derived from the same individual for whom the diagnosis is being performed, but at a different time-point, for example, a week, month, year or several years earlier. As such, the control profile may also include the level of the one or more cytokines or inflammatory biomarkers in the individual before the individual was considered to be at risk of early stage organ damage caused by inflammation associated with infection (such as prior to being diagnosed with infection). Such a control profile thereby forms a baseline or basal level profile of the level of the one or more cytokines or inflammatory biomarkers in the individual, against which the test profile may be compared.

A control profile for monitoring or determining treatment efficacy may be generated from the same individual receiving idronoxil, or derivative, pharmaceutically acceptable salt, ester, amide, polymorph and/or prodrug thereof, but at a different time-point, for example, a week, month or several months earlier. Such a control profile thereby forms a baseline or basal level profile in the individual of the level of the one or more cytokines or inflammatory biomarkers in the individual prior to disease symptoms or at a stage prior to or during the idronoxil, or derivative, pharmaceutically acceptable salt, ester, amide, polymorph and/or prodrug thereof therapy.

Laboratory based methods for measuring levels of cytokines or inflammatory biomarkers indicative of early stage organ damage caused by inflammation associated with infection will be known to the skilled person. These methods will be useful in the methods of the present invention, for example, for determining whether an individual is suffering from early stage organ damage caused by inflammation associated with infection and also to determine whether the treatment in accordance with the present invention has been successful.

A variety of methods for determining cytokine levels in biological samples, including serum and plasma samples are known to the skilled person. Briefly, the levels of inflammatory cytokines can be determined in biological samples by enzyme-linked immunosorbent assays (ELISAs) using ELISA kits according to manufacturer's protocols.

Alternatively, levels of cytokines or inflammatory biomarkers can be determined using multiplex bead array kits in accordance with the manufacturer's instructions (for example, Bio-Plex Human Cytokine Assay).

The skilled person will also appreciate that baseline inflammatory cytokine levels can be very high in certain individuals, due to their underlying infection. Accordingly, the skilled person will also appreciate that determining fold increases, net increases or rate of change increases in cytokine or inflammatory biomarker levels may provide a better indication of the likelihood of early organ damage in an individual, and successful treatment, rather than absolute levels.

Other methods of determining likelihood of early organ damage include monitoring of proteins which are indicative of elevated cytokine or inflammatory biomarker levels. For example, C-reactive protein (CRP) is an acute phase protein produced by the liver and which can often serve as a reliable surrogate for IL-6 bioactivity. Accordingly, the skilled person will also appreciate the utility in measuring CRP levels as a means for identifying an individual in need of treatment for early stage organ damage caused by inflammation associated with infection.

Preferably, wherein the infection is caused by SARS-CoV-2, symptoms of early stage organ damage identified by biochemical or clinical tests known to those skilled in the art include one or more of:

temperature greater than about 38° C., heart rate greater than about 90 beats/min, respiratory rate greater than about 20 breaths/min and/or arterial $pCO_2$ less than 32 mmHg, procalcitonin (PCT) level below about 0.1 ng/mL, preferably between about 0.05 and about 0.1 ng/mL, D-dimer level greater than about 1 ug/mL, preferably between about 1-2.5 ug/mL, C reactive protein level greater than 3 mg/L, preferably between about 3-25 mg/L, IL-2R level greater than about 333 U/mL, preferably between about 333 and about 630 U/mL, IL-6 level greater than about 1.7 pg/mL, preferably between about 1.7 pg/mL and about 15 pg/mL, IL-8 level greater than about 9 pg/mL, preferably between about 9 pg/mL and about 30 pg/mL, IL-10 level greater than about 3 pg/mL, preferably between about 3 pg/mL and about 5 pg/mL, TNF level greater than about 3 pg/mL, preferably between about 3 pg/mL] and about 9.5 pg/mL, Beta 2 Microglobulin (B2M) level greater than 3 ug/mL, Arterial oxygen tension (Pao$_2$) less than 80 mmHg, and/or cardiac troponin I level greater than about 0.05 ng/mL;

white blood cell count below about 10.0×10$^9$/L, lymphocyte cell count below about 2.0×10$^9$/L, preferably between about 0.9-1.6×10$^9$/L, abnormally low counts of T lymphocyte subsets including one or more of: CD3+ T-cell (<200/pL), CD4+ T-cell (<100/pL), CD8+ T-cell (<100/pL), B-cell (<50/pL), and combinations thereof;

elevated levels of one or more of: IL-1β, lactate, and HMGB1, ALT, AST, creatinine, CK, LDH, N-terminal pro-brain natriuretic peptide, and combinations thereof;

CRP (R=0.62, p<0.01);

erythrocyte sedimentation rate (ESR) (R=0.55, p<0.01);

granulocyte/lymphocyte ratio (R=0.49, p<0.01); and/or serum ferritin levels above about 400 ng/mL.

Preferably, an individual identified, diagnosed, or suspected of having, early stage organ damage is not identified, diagnosed, or suspected of having late stage organ damage. Preferably, an individual identified, diagnosed, or suspected of having, one or more symptoms of early stage organ damage is not identified, diagnosed, or suspected of having one or more symptoms of late stage organ damage.

Preferably, wherein the infection is caused by SARS-CoV-2, symptoms of early stage organ damage may be identified between about 7-10 days after onset of infection, including 7, 8, 9 or 10 days after onset of infection.

An individual may be identified as experiencing a symptom of early stage organ damage by biochemical or clinical methods or tests known to those skilled in the art.

Common causes of sepsis include pneumonia, an infection of the digestive system (which includes organs such as the stomach and colon), an infection of the kidney, bladder and other parts of the urinary system, or a bloodstream infection (bacteremia). Therefore a subject in need thereof may be diagnosed with one of these conditions.

Sepsis and septic shock are more common in the following subjects:

Are very young or very old;

Have a compromised immune system, i.e. "immunocompromised subject";

Have diabetes or cirrhosis;

Are already very sick, often in a hospital intensive care unit;

Have wounds or injuries, such as burns;

Have invasive devices, such as intravenous catheters or breathing tubes; and

Have previously received antibiotics or corticosteroids.

A "subject" as defined herein, in other words a subject in need thereof, may be any one of the subjects listed immediately above.

Late stage organ damage caused by inflammation associated with infection refers to organ dysfunction associated with sepsis. Symptoms of late stage organ damage caused by inflammation include but are not limited to: low blood oxygen, widened pulse pressure, increased cardiac output (early), potentially diminished cardiac output (late), reduced carbon dioxide (PaCO$_2$) level in the blood, high nitrogen levels in blood, low urine production, elevated transaminases, factor I deficiency, excessive bleeding, higher-than-normal level of bilirubin, bluish discoloration of the digits and lips(cyanosis), severe problems breathing, acute confusion, aphasia, and combinations thereof. Preferably, the individual is not identified, diagnosed with, or suspected of having 1, 2, 3, 4, 5, 6, or more symptoms of late stage organ damage caused by inflammation.

Symptoms of late stage organ damage caused by inflammation identified by biochemical or clinical tests known to those skilled in the art may include, but are not limited to one or more of:

neutrophil cell count above about 8.0×10$^9$/L, preferably above about 10×10$^9$/L, lymphocyte cell count below about 0.9×10$^9$/L, platelet cell count below about 150×10$^9$/L, procalcitonin PCT level above about 0.1 ng/mL, D-dimer level above about 2.6 ug/mL, C reactive protein level greater than 25 mg/mL, preferably greater than 50 mg/L, more preferably greater than 100 mg/L, IL-2R level great than about 630 U/mL, IL-6 level great than about 15 pg/mL, IL-8 level great than about 30 pg/mL, IL-10 level great than about 5 pg/mL, TNF level great than about 9.5 pg/mL, creatinine level greater than about 87.5 μmol/L, lactate level greater than about 1.5 mmol/L, preferably greater than about 2.0 mmol/L, about 3.0 mmol/L or about 4.0 mmol/L, and/or elevated levels of one or more of: bilirubin, IL-1ra, protein C, neutrophil gelatinase-associated lipocalin (NGAL), CD64, and sTREM-1.

Preferably, wherein the infection is caused by SARS-CoV-2, symptoms of late stage organ damage caused by inflammation may be identified about 10 days after onset of infection, including 10-22 days after onset of infection, including 10, 11, 12, 13, 14, 15, 16, 17, 18, 19, 20, 21 or 22 days after onset of infection.

An individual identified, diagnosed, or suspected of having, late stage organ damage, or a symptom thereof, may have one or more symptoms of early stage organ damage.

Preferably an individual identified, diagnosed, or suspected of having, inflammation characterised as prior to late stage organ damage, does not have a symptom of late stage organ damage caused by inflammation.

Severe sepsis is sepsis with impaired blood flow to body tissues (hypoperfusion) or detectable organ dysfunction. Severe sepsis may occur with or without sepsis-induced hypotension (e.g., with fever, encephalopathy and renal failure but a normal blood pressure).

Septic shock is severe sepsis with sepsis-induced hypotension [systolic blood pressure <90 mm Hg (or a drop of >40 mm Hg from baseline) or mean arterial pressure <70 mm Hg] that persists after adequate fluid resuscitation. "Adequate" is determined by the estimation of the patient's pre-sepsis intravascular volume status.

Sepsis is most common and most dangerous in older adults, pregnant women, children younger than 1, people who have chronic conditions, such as diabetes, kidney or lung disease, or cancer, and people who have weakened immune systems. A subject in need thereof may be any one of these individuals.

The infection may be caused by bacteria, fungi, viruses, or protozoa. Preferably, the infection is caused by bacteria or viruses. Laboratory based methods for diagnosing an individual infected with a bacterium, fungus, virus, or protozoan will be known to the skilled person. For example, a clinical diagnosis of SARS-CoV-2 virus infection may include a positive nucleic acid test from a sample of an individual, wherein the sample is from respiratory tissue, blood, plasma or other bodily fluid.

In one embodiment, the infection is caused by a virus. The virus is preferably selected from: coronavirus, influenza, parainfluenza, respiratory syncytial virus (RSV), adenovirus, cytomegalovirus (CMV), Epstein-Barr virus (EBV), varicella zoster virus (VZV), dengue virus, rhinovirus, Herpes simplex virus and enteroviruses. More preferably, the virus is coronavirus or influenza. Even more preferably, the virus is severe acute respiratory syndrome coronavirus (SARS-CoV), Middle East respiratory syndrome coronavirus (MERS-CoV), or severe acute respiratory syndrome coronavirus 2 (SARS-CoV-2), most preferably SARS-CoV-2.

In an alternative preferred embodiment, the infection is caused by bacteria. The bacteria are preferably selected from: *Streptococcus* spp., *Escherichia coli, Pseudomonas aeruginosa, Haemophilus influenza, Klebsiella pneumoniae*, and *Acinetobacter baumannii* and *Neisseria meningitidis*. *Streptococcus* spp. includes, but is not limited to, *Staphylococcus aureus, Streptococcus pyogenes*, and *Streptococcus pneumoniae*. In one embodiment, wherein the infection is caused by bacteria, the individual is diagnosed with or suspected of having a viral infection. Preferably the viral infection is caused by a virus selected from: coronavirus, influenza, parainfluenza, respiratory syncytial virus (RSV), adenovirus, cytomegalovirus (CMV), Epstein-Barr virus (EBV), varicella zoster virus (VZV), dengue virus, rhinovirus, Herpes simplex virus and enteroviruses. More preferably, the viral infection is caused by coronavirus or influenza. Even more preferably, the viral infection is caused by severe acute respiratory syndrome coronavirus (SARS-CoV), Middle East respiratory syndrome coronavirus (MERS-CoV), and severe acute respiratory syndrome coronavirus 2 (SARS-CoV-2), most preferably SARS-CoV-2

In another embodiment the infection may be caused by fungi. The fungi are preferably selected from *Candida* and *Aspergillus*. *Candida* includes but is not limited to *Candida albicans, Candida tropicalis, Candida glabrata*, and *Candida parapsilosis*.

In another embodiment the infection may be caused by protozoa. The protozoa are preferably selected from: *Plasmodium, E. vermicularis, Trypanosoma cruzi*, Echinococcosis, Cysticercosis, Toxocaiasis, Tiichomoniasis, and Amebiasis.

Successful treatment may be determined by:

treatment of, or a decrease in the severity of one or more symptoms of, early stage organ damage caused by inflammation associated with infection, including but not limited to: reduction in fever, increased blood oxygen levels, reduction in level of one or more cytokines or inflammatory biomarkers (preferably selected from IP-10, IL-6, IFN-β and TNF-α), reduction in clotting factor levels, reduction in blood clotting, and combinations thereof;

prevention of, or decrease in the severity of one or more symptoms of, late stage organ damage or sepsis caused by inflammation associated with infection; and/or an increase in survival time.

Idronoxil

Idronoxil (IDX), otherwise known as phenoxodiol; dehydroequol; Haginin E (2H-1-Benzopyran-7-0,1,3-(4-hydroxyphenyl)), has the following structure:

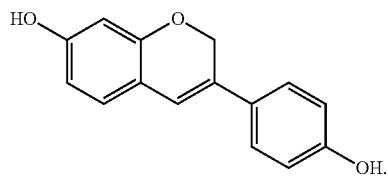 [SMILES: Oc1ccc(C2=Cc3ccc(O)cc3OC2)cc1]

Unless the context requires otherwise, use herein of the term idronoxil includes reference to any idronoxil derivative, or pharmaceutically acceptable salt, ester, amide, polymorph and/or prodrug thereof.

Methods for synthesis of idronoxil are described in WO1998/008503 and WO2005/049008 and references cited therein towards the synthesis, the contents of which are incorporated herein by reference in entirety.

Compositions, Formulations and Modes of Administration

The phrase "therapeutically effective amount" generally refers to an amount of one or more active ingredients of the invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

Typically, a therapeutically effective dosage is formulated to contain a concentration (by weight) of at least about 0.1% up to about 50% or more, and all combinations and subcombinations of ranges therein. The compositions can be formulated to contain one or more actives described herein in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30%. Exemplary compositions may contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 16, 15, 14, 13, 12, 11 or 10%. The compositions can contain from greater than about 1% for example, about 2%, to less than about 10%, for example about 9 or 8%, including concentrations of greater than about 2%, for example, about 3 or 4%, to less than about 8%, for example, about 7 or 6%. The active agent can, for example, be present in a concentration of about 5%. In all cases, amounts may be adjusted to compensate for differences in amounts of active ingredients actually delivered to the treated cells or tissue.

The frequency of administration may be once daily, or 2 or 3 time daily. The treatment period may be for the duration of the detectable disease. Preferably, the treatment is for a period of 14 to 28 days.

Compositions of the invention may be administered orally, nasally, intravenously, intramuscularly, topically, subcutaneously, rectally, vaginally or by urethral application. Preferably, compositions of the invention are administered rectally, vaginally or by urethral application.

Pharmaceutical compositions of the invention typically include a therapeutically effective amount of one or more active ingredients in admixture with one or more pharmaceutically and physiologically acceptable formulation materials. Suitable formulation materials include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial perilymph, possibly supplemented with other materials common in compositions for parenteral administration. Neutral buffered saline or saline mixed with serum albumin are further exemplary vehicles.

Pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminium hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as colouring agents, releasing agents, coating agents, sweetening, flavouring and perfuming agents, preservatives and antioxidants can also be present in the composition, according to the judgment of the formulator.

Various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as arachis oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or arachis oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monoleate, and condensation products of partial esters derived from fatty acids and hexitol with ethylene oxide such as polyoxyethylene sorbitan monooleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S. P. and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

A pharmaceutical composition may be formulated as inhaled formulations, including sprays, mists, or aerosols. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers.

Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Compositions suitable for rectal administration are preferably presented as unit dose suppositories. These may be prepared by at least partially dispersing the active in one or more lipophilic bases and then shaping the mixture.

In certain embodiments the therapeutic composition may be provided in the form of a device, disposable or reusable, including a receptacle for holding the therapeutic, or pharmaceutical composition. In one embodiment, the device is a syringe. The device may hold 1-2 mL of the therapeutic composition. The therapeutic composition may be provided in the device in a state that is ready for use or in a state requiring mixing or addition of further components.

It is envisioned that the continuous administration or sustained delivery of idronoxil, or derivative, pharmaceutically acceptable salt, ester, amide, polymorph and/or prodrug thereof may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the active which have the effect of continuous presence, in predictable amounts, based on a determined dosage regimen. Thus, idronoxil includes idronoxil derivatized or otherwise formulated to effectuate such continuous administration.

Pharmaceutical compositions may be formulated as sustained release formulations such as a capsule that creates a slow release of active following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of active release. The amount of active contained within a sustained release formulation depends upon, for example, the site of implantation, the rate and expected duration of release and the nature of the condition to be treated.

In one embodiment, the idronoxil, or derivative, pharmaceutically acceptable salt, ester, amide, polymorph and/or prodrug thereof is administered in a composition including a lipophilic base for use in a device for rectal, vaginal or urethral application; a surfactant; and idronoxil, or derivative, pharmaceutically acceptable salt, ester, amide, polymorph and/or prodrug thereof.

In this disclosure, 'base' may refer to a substance commonly used as a carrier in a suppository, pessary or intraurethral device. Generally the base has a solvent power for the idronoxil, or derivative, pharmaceutically acceptable salt, ester, amide, polymorph and/or prodrug thereof enabling at least partial, preferably complete dispersion of the idronoxil, or derivative, pharmaceutically acceptable salt, ester, amide, polymorph and/or prodrug thereof in the base.

The base may be comprised of, or consist of an oil or fat. The base may be a blend of oils or fats. The oil or fat may be esterified with glycerol. The oil or fat may be interesterified.

The base may be formed or derived from a hydrogenated oil or fat. The oil or fat may be substantially or completely hydrogenated. The base may be derived from a synthetic oil. The base may derived from a natural or synthetic oil or fat. The base may be substantially comprised of mono-, di-, tri-glycerides, preferably substantially tri-glycerides.

The base may be a hard fat. Hard fats can be made from substantially hydrogenated oils through esterification with glycerol, or by interesterification. The oil may be completely hydrogenated, or partially hydrogenated. Hard fats are characterised by their melting point, hydroxyl value and saponification value. Hard fats are typically solid at room temperature. The base may comprise mono, di and/or triglycerides. Preferably the base substantially comprises triglycerides. The base may be derived from natural oils such as canola oil, palm oil, palm kernel oil, soya bean oil, vegetable oil, castor oil, and combinations thereof. Oils derived from these sources may be fractionated to obtain oil fractions containing saturated fatty acids.

The base may be formed from synthetic oils or fats, examples including Fattibase, Wecobee, Witepsol (Dynamit Nobel, Germany), Suppocire (Gattefosse, France), Hydrokote and Dehydag.

A base may comprise a hard fat comprising esterified or non-esterified fatty acid chains. Preferably the base is substantially esterified. Preferably the base consists essentially of esterified fatty acid chains. Most preferably the base is completely esterified. The fatty acid chains may be in the form of mono, di and/or trigycerides, preferably C10-C18 triglycerides. The tri-ester fraction may be predominant.

The percentage of the triglyceride fraction may be about 50%, about 70%, about 80%, about 90%, about 95%, about 96%, about 97%, about 98%, about 99%, or about 99.9%. The triglyceride fraction may be from about 70%-99.9%. The hard fat may consist substantially of triglycerides. The hard fat may consist essentially of triglycerides.

The base may be completely or substantially insoluble in water.

The base may be a hard fat, and have a defined hydroxyl value. The hydroxyl value of a hard fat is a measure of the context of free hydroxyl groups in a chemical substance, and is typically expressed in units of milligrams of KOH per gram of substance equivalent to the hydroxyl content. The base may have a hydroxyl value of less than 15. The hydroxyl value indicates the amount of mono and/or di glycerides in the base. A hydroxyl value close to 0 indicates the hard fat is comprised essentially of triglycerides. Preferably the base may have a hydroxyl value of less than 5. Preferably the base may have a hydroxyl value of about 5. Preferably the base may have a hydroxyl value of 5. Preferably the base may have a hydroxyl value of close to 0.

The base may be a hard fat and have a defined melting point. The base may have a melting point of approximately body temperature. The base may have a melting point of about 30 to about 40° C. or any range therein, including about 30° C., about 35° C., about 37° C. or about 40° C. The base may have a melting point of about 35° C. to about 40° C. Preferably the melting point of the base is about 38° C. to about 40° C. More preferably the melting point of the base is about 38° C. to about 39° C.

The base has a saponification value. The saponification value of the base is a measure of the number of milligrams of potassium hydroxide required to saponify 1 g of the base. The saponification value of the base may be from about 210 to 260.

In one preferred embodiment the base is Suppocire CM. Suppocire CM consists of mono-, di and triglyceride esters of fatty acids, the triester fraction being predominant. Suppocire CM consists substantially of triglycerides. Suppocire CM has a melting point approximately equal to body temperature.

The proportion of the lipophilic suppository base in the final product is a function of the dosage of active pharmaceutical ingredient and the presence of other pharmaceutical or inert ingredient (if any) but may be provided by way of example in an amount of about 1 to 99% w/w formulation.

The surfactant used may be a single surfactant, or a surfactant blend of more than one surfactant.

A surfactant is an amphiphilic molecule, it may be comprised of a head and a tail or it may be comprised of multiple blocks wherein each block has a different hydrophobicity or hydrophilicity. The different solubilities of the parts of the molecule allow the surfactant to preferentially arrange itself at the interface between two phases and lower the surface tension, or interfacial energy.

Preferably the surfactant is non-ionic.

The surfactant has a hydrophobic-lipophilic balance. The hydrophilic-lipophilic balance is also called HLB. Those skilled in the art will be familiar with the HLB. The HLB is an estimation of the relative size and strength of the head and the tail of the surfactant on a scale from 0 to 20.

The HLB of the surfactant(s) may be between about 6 and about 13 or any range therein. The HLB of the surfactant(s) may be 6, 7, 8, 9, 10, 11, 12 or 13. The HLB of the surfactant(s) may be about 6, about 7, about 8, about 9, about 10, about 11, about 12 or about 13.

The surfactant(s) may show inverse aqueous solubility characteristics with increasing temperature.

The surfactant(s) used may be a polyethylene glycol stearate. The surfactant may be a monosterate, or a disterate or a mixture of both. The surfactant may include free glycols. The average molecular weight of the polymer chain, may be indicated in the name of the specific substance e.g. Polyethylene-glycol-100 stearate is a polyethylene glycol of approximately 100 g/mol attached to a stearic acid. The average number of ethoxylated groups attached in the polymer chain may be indicated in the name of the specific substances, e.g. Polyethylene-glycol-8 is a polymer chain with an average of 8 ethoxy groups. Polyethylene glycol may be abbreviated as PEG.

The surfactant may have an average number of PEG groups of about 5 to about or any range within. The surfactant may have an average number of 5 PEG groups, 6 PEG groups, 7 PEG groups, 8 PEG groups, 9 PEG groups, 10 PEG groups, 11 PEG groups, 12 PEG groups, 13 PEG groups, 14 PEG groups, 15 PEG groups. Preferably the surfactant has 8 PEG groups.

The surfactant may be a polyethylene glycol esterified with caprylic acid, capric acid, lauric acid, lyristic acid, palmitic acid, stearic acid, arachidic acid, behenic acid, lignoceric acid or cerotic acid, or a blend thereof. The surfactant may be a monoester or a diester or a mixture of mono and di esters. Preferably the surfactant is a stearic ester. In one embodiment the surfactant is Polyglycol-8 stearate. PEG-8-stearate may be a mono-stearate of a distearate, referred to respectively as PEG8MS or PEG8DS. Polyethylene glycol stearates may be obtained from various commercial sources, in various grades, under various tradenames, for example Cithrol4DS (PEG8DS, Croda) and Myrj S8 (PEG8MS, Croda).

Preferably the surfactant is PEG8MS.

The dispersion of the idronoxil, or derivative, pharmaceutically acceptable salt, ester, amide, polymorph and/or prodrug thereof in the lipophilic base with the surfactant advantageously improves the release profile of the idronoxil, or derivative, pharmaceutically acceptable salt, ester, amide, polymorph and/or prodrug thereof. The release of the idronoxil, or derivative, pharmaceutically acceptable salt, ester, amide, polymorph and/or prodrug thereof from the base is influenced by the surfactant used. The surfactant may be chosen such that the release profile of the active is substantially the same, as the release profile obtained with PEG-8-MS.

The surfactant may be chosen such that it is capable of forming or aiding the formulation of an emulsion with the liquefied lipophilic base and water within the rectum.

The composition may comprise any amount of surfactant effective to improve the transfer of the idronoxil, or derivative, pharmaceutically acceptable salt, ester, amide, polymorph and/or prodrug thereof across the mucosal membrane. The proportion of the surfactant in the final product is a function of the dosage of active pharmaceutical ingredient and the presence of other pharmaceutical or inert ingredient (if any) but may be provided by way of example in an amount of about 1 to 99% w/w formulation. The proportion of the surfactant in the final product expressed as a percentage of the base, may be from about 2 to about 50% or any range therein including about 2%, about 5%, about 8%, about 10%, about 15%, about 20%, about 22%, about 25%, about 30%, about 35%, about 40%, about 45%, or about 50%. The proportion of the surfactant in the final product expressed as a percentage of the base, may be from 2 to 50% or any range therein including 2%, 5%, 8%, 10%, 15%, 20%, 22%, 25%, 30%, 35%, 40%, 45%, or about 50%. For example a formulation using a hard fat base with 50% surfactant and 18.5% active would have a total composition of 18.5% active, 40.75% surfactant and 40.75% hard fat.

In one embodiment the surfactant used is PEG-8-MS. The proportion of the PEG-8-MS in the base is from about 5% to about 20%. Preferably the proportion is about 8%. Preferably the proportion is 8%.

In another embodiment the surfactant used is PEG-8-DS. When the surfactant used is PEG8DS the proportion of the surfactant in the base is from about 15-50%, preferably about 22%. Preferably the proportion is 22%. In another embodiment the proportion of surfactant in the base is preferably about 50% or 50%.

The suppository, pessary and devices for urethral application of the invention may be prepared as follows. The idronoxil, or derivative, pharmaceutically acceptable salt, ester, amide, polymorph and/or prodrug thereof is contacted with a suppository base (as described above) in molten form in conditions enabling at least partial, preferably complete or substantially complete dispersion of the idronoxil, or derivative, pharmaceutically acceptable salt, ester, amide, polymorph and/or prodrug thereof in the base. This solution is then poured into a suitable mould, such as a PVC, polyethylene, or aluminium mould. For example, the idronoxil, or derivative, pharmaceutically acceptable salt, ester, amide, polymorph and/or prodrug thereof may be contacted with the base at a temperature of from about 35° C. to about 60° C. and preferably from about 55° C. to about 60° C. Preferably the idronoxil, or derivative, pharmaceutically acceptable salt, ester, amide, polymorph and/or prodrug thereof is contacted with the base at a temperature of 20° C. above the melting point of the base. The idronoxil, or derivative, pharmaceutically acceptable salt, ester, amide, polymorph and/or prodrug thereof can be milled or sieved prior to contact with the base.

It will be understood that the method for manufacture of the formulation and devices formed from same of the invention require a dispersion of the idronoxil, or derivative, pharmaceutically acceptable salt, ester, amide, polymorph and/or prodrug thereof in the suppository base so that the idronoxil, or derivative, pharmaceutically acceptable salt, ester, amide, polymorph and/or prodrug thereof is at least partially dispersed therein. In one embodiment, the conditions provided for manufacture, and formulation or device formed from same, enable at least, or provide at least, 50%, preferably 60%, preferably 70%, preferably 80%, preferably 90%, preferably 95% of the idronoxil, or derivative, pharmaceutically acceptable salt, ester, amide, polymorph and/or prodrug thereof for a given dosage unit to be dispersed in the dosage unit. In these embodiments, no more than 50% of the idronoxil, or derivative, pharmaceutically acceptable salt, ester, amide, polymorph and/or prodrug thereof for a given dosage unit, preferably no more than 40%, preferably no more than 30%, preferably no more than 20%, preferably no more than 10%, preferably no more than 5% of idronoxil, or derivative, pharmaceutically acceptable salt, ester, amide, polymorph and/or prodrug thereof for a given dosage unit may be in admixture with, (i.e. undispersed in) the suppository base of the dosage unit.

In a preferred embodiment the base used for the manufacture of the suppository is a hard fat, and is solid at room temperature. The hard fat is melted to a maximum temperature of approximately 20° C. above the melting temperature of the fat. The melting temperature of the fat is preferably body temperature. The temperature is controlled during the manufacturing process such that the base is kept at the lowest possible temperature when the active and surfactant is introduced. Following introduction and stirring of the active the composition is cooled to the maximum possible cooling temperature. The control of the temperature advantageously reducing the post hardening of the suppository. Control of the temperature of the manufacturing process also increases homogeneous distribution of the active within the base. Overheating of the hard fat base modifies the crystal structure of the fat which also impacts the distribution of active and potential release profile of the active from the composition.

The manufactured suppository may be in a glassy solid state or a semi-crystalline state, preferably glassy solid state. The solid form of the base may be characterised by DSC or XRD.

In a preferred embodiment, all of the idronoxil, or derivative, pharmaceutically acceptable salt, ester, amide, polymorph and/or prodrug thereof added to a dosage unit is dispersed in the base. The dosage unit may contain the idronoxil, or derivative, pharmaceutically acceptable salt, ester, amide, polymorph and/or prodrug thereof from about 0.1 to about 50% w/w. The dosage unit may contain the idronoxil, or derivative, pharmaceutically acceptable salt, ester, amide, polymorph and/or prodrug thereof from about 5% about 6% about 7% about 8% about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%—all % w/w. Preferably the dosage unit may be from about 15 to about 20% or any range therein. The dosage unit may be about 15.5%, about 16.5%, about 17.5% about 18.5%, or about 19.5%. In this embodiment, no idronoxil, or derivative, pharmaceutically acceptable salt, ester, amide, polymorph and/or prodrug thereof is left in admixture with the suppository base. This is believed to increase the likelihood of the uptake of all of the idronoxil, or derivative, pharmaceutically acceptable salt, ester, amide, polymorph and/or prodrug thereof given in the dosage unit.

It will be understood that the objective of the manufacture process is not to admix, or to mingle, or to blend the suppository base with the idronoxil, or derivative, pharmaceutically acceptable salt, ester, amide, polymorph and/or prodrug thereof as generally occurs in pharmacy practice of admixing components, as it is believed that the resulting admixture would have a lower likelihood of providing therapeutic benefit. In this context, it is particularly important that any other excipient, carrier or other pharmaceutical active does not adversely interfere with the dispersion of the idronoxil, or derivative, pharmaceutically acceptable salt, ester, amide, polymorph and/or prodrug thereof in the base, for example as may occur if the idronoxil, or derivative, pharmaceutically acceptable salt, ester, amide, polymorph and/or prodrug thereof forms a complex with a charged molecular species (other pharmaceutical active, carrier or excipient), the result of which would be to decrease the propensity of the complex, and therefore the idronoxil, or derivative, pharmaceutically acceptable salt, ester, amide, polymorph and/or prodrug thereof contained in it, to disperse in the suppository base.

Optionally the suppositories, pessaries or intra-urethral devices may be coated, prior to packing, for example with cetyl alcohol, macrogol or polyvinyl alcohol and polysorbates to increase disintegration time or lubrication or to reduce adhesion on storage.

One or more sample suppositories, pessaries, or intra-urethral devices from each batch produced are preferably tested by a dissolution method for quality control. Preferably, a sample from each batch is tested in vitro, preferably using a method described herein, to determine whether greater than 75% of the idronoxil, or derivative, pharmaceutically acceptable salt, ester, amide, polymorph and/or prodrug thereof dissolves from the suppository, pessary, or intra-urethral device within 6.5 hours.

Typically the suppository, or pessary device is substantially hydrophobic or lipophilic throughout and does not contain a hydrophilic substance such as hydrophilic carrier or pharmaceutical active, or hydrophilic foci or region formed from the ligation or complexing of the idronoxil, or derivative, pharmaceutically acceptable salt, ester, amide, polymorph and/or prodrug thereof to or with another pharmaceutical compound, carrier or excipient.

Preferably the formulation for forming the suppository, pessary and devices for urethral application does not include a further pharmaceutical active, cytotoxic or chemotherapeutic agent. In this embodiment, the only active is the idronoxil, or derivative, pharmaceutically acceptable salt, ester, amide, polymorph and/or prodrug thereof and the formulation does not include a platin, taxane or other cytotoxic or chemotherapeutic agent.

The total weight of the suppository preferably ranges from about 2000 to about 3500 mg and more preferably from about 2200 to about 3300 mg. According to one embodiment, the suppository has a total weight ranging from about 2200 mg to about 3300 mg.

The suppository or pessary is preferably smooth torpedo-shaped.

The melting point of the suppository or pessary is generally sufficient to melt in the patient's body, and is typically no more than about 37° C.

Dosing

The effective amounts and method of administration of the present invention can vary based on the individual, what condition is to be treated and other factors evident to one skilled in the art. It will be understood, that the specific dose level for any particular patient will depend upon a variety of factors including the activity of the specific compound employed, the age, body weight, general health, sex, diet, time of administration, route of administration, number of doses, and rate of excretion, drug combination (i.e. other drugs being used to treat the patient), and the severity of the particular disorder undergoing therapy.

Idronoxil, or derivative, pharmaceutically acceptable salt, ester, amide, polymorph and/or prodrug thereof, may be administered in an amount of 400 mg-1800 mg daily, preferably 400 mg, 600 mg, 800 mg, 1200 mg, 1600 mg, or 1800 mg daily, more preferably 1200 mg-1800 mg daily.

Preferably, idronoxil, or derivative, pharmaceutically acceptable salt, ester, amide, polymorph and/or prodrug thereof, is administered rectally, vaginally or by urethral application, for example in the form of a suppository. The total weight of the suppository preferably ranges from about 2000 to about 3500 mg and more preferably from about 2200 to about 3300 mg. According to one embodiment, the suppository has a total weight ranging from about 2200 mg to about 3300 mg. Each suppository comprises:

400 mg or 600 mg of idronoxil, or derivative, pharmaceutically acceptable salt, ester, amide, polymorph and/or prodrug thereof;

a surfactant;

a suppository base in the form of an oil or fat;

wherein the suppository base is provided an amount of 1-99% w/w of the suppository.

In one particularly preferred embodiment, idronoxil, or derivative, pharmaceutically acceptable salt, ester, amide, polymorph and/or prodrug thereof, may be contained in the suppository in an amount of 400 mg or 600 mg. An individual may be administered a plurality of suppositories once daily, twice daily, or three times daily to provide the individual with a total daily dosing of idronoxil, or derivative, pharmaceutically acceptable salt, ester, amide, polymorph and/or prodrug thereof, in an amount of 400 mg, 600 mg, 800 mg, 1200 mg, 1600 mg, or 1800 mg.

Preferably, idronoxil, or derivative, pharmaceutically acceptable salt, ester, amide, polymorph and/or prodrug thereof, is administered for a period of 14 to 28 days, including 14 days, 15 days, 16 days, 17 days, 18 days, 19 days, 20 days, 21 days, 22 days, 23 days, 24 days, 25 days, 26 days, 27 days, and 28 days.

Idronoxil, or derivative, pharmaceutically acceptable salt, ester, amide, polymorph and/or prodrug thereof, may be given once, twice or three times daily for a period of 2 to 4 weeks.

Preferably the individual has not been administered idronoxil, or derivative, pharmaceutically acceptable salt, ester, amide, polymorph and/or prodrug thereof at the onset of infection.

Preferably the individual has not been administered idronoxil, or derivative, pharmaceutically acceptable salt, ester, amide, polymorph and/or prodrug thereof at the onset of inflammation.

Preferably, administration consists essentially of, or consists of the period from early stage organ damage to prior to late stage organ damage caused by inflammation and/or sepsis.

Preferably, idronoxil, or derivative, pharmaceutically acceptable salt, ester, amide, polymorph and/or prodrug thereof, is administered no less than 7 days after the onset of inflammation. Idronoxil may be administered 7 days, 8 days, 9 days, 10 days, 11 days, 12 days, 13 days, 14 days, 15 days, 16 days, 17 days, 18 days, 19 days, 20 days, 21 days or 22 days after the onset of inflammation. More preferably, idronoxil is administered 7 days, 8 days, 9 days, or 10 days after the onset of inflammation.

Kit

In another embodiment there is provided a kit or article of manufacture including one or more compositions, and/or pharmaceutical compositions as described above.

In other embodiments there is provided a kit for use in a therapeutic application mentioned above, the kit including:
 a container holding one or more compositions and/or pharmaceutical compositions as described herein;
 a label or package insert with instructions for use.

In certain embodiments the kit may contain one or more further active principles or ingredients for treatment of inflammation associated with infection as described herein.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat an inflammatory disease or condition described herein.

The kit may comprise (a) a therapeutic composition; and (b) a second container with a second active principle or ingredient contained therein. The kit in this embodiment of the invention may further comprise a package insert indicating the composition and other active principle can be used to treat a disorder or prevent a complication stemming from an inflammatory disease described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It will be understood that the invention disclosed and defined in this specification extends to all alternative combinations of two or more of the individual features mentioned or evident from the text or drawings. All of these different combinations constitute various alternative aspects of the invention.

EXAMPLES

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

Methods:

Cell culture and reagents. HEK cells stably expressing the murine STING fused to an N-terminal mCherry-tag and L929 expressing an interferon stimulated response element (ISRE)-Luciferase were previously described (3). Immortalised mouse Bone Marrow derived Macrophages (iBMMs) and THP-1 cells stably expressing an inducible R284S mutant of human STING were previously described (4). TC-1 (5), HEK, L929 and iBMMs were grown in Dulbecco's modified Eagle's medium (Life Technologies) supplemented with 10% sterile fetal bovine serum (Life Technologies) and 1×antibiotic/antimycotic (Life Technologies) (referred to as complete DMEM). PC-3 (CRL-1435), HOS (CRL-1543) and MG-63 (CRL-1427) were purchased from the ATCC. MG-63 and HOS were grown in ATCC-formulated Eagle's Minimum Essential Medium supplemented with 10% sterile fetal bovine serum (Life Technologies) and 1×antibiotic/antimycotic (Life Technologies) (referred to as complete EMEM). PC-3 were grown in ATCC-formulated F-12K Medium supplemented with 10% sterile fetal bovine serum (Life Technologies) and 1× antibiotic/antimycotic (Life Technologies) (referred to as complete F12K).

Human fibroblasts (hTERT-BJ1 cells) were grown in complete DMEM supplemented with sodium pyruvate (Life technologies). THP-1 were grown in RPMI (Life Technologies) supplemented with 10% sterile fetal bovine serum (Life Technologies) and 1×antibiotic/antimycotic (Life Technologies) (referred to as complete RPMI). Media of THP-1 and iBMMs were supplemented with Puromycin (Sigma) to ensure selection of pTRIPZ-hSTING R284S (4). Trex1-mutant mice (used under animal ethics ref. A2018/38) have a single-based mutation in Trex1 leading to a premature stop codon (Q169X) and aberrant accumulation of cytoplasmic DNA, resulting in basal engagement of the cGAS-STING pathway (Ellyard J. I. and Vinuesa C. G., manuscript in preparation), similar to that reported in Trex1-deficient mice. Primary bone marrow derived macrophages (BMDMs) from 3 Trex1-mutant mice were extracted and differentiated for 6 days in complete DMEM supplemented with L929 conditioned medium as previously reported (6).

Primary blood mononuclear cells (PBMCs) from healthy donors were collected and purified as previously published (7).

DMXAA (Sigma D5817), H151 (Invivogen), and camptothecin (Sigma catalog no. C9911) were resuspended in DMSO. Idronoxil (IDX) was provided by Noxopharm LTD and resuspended as a stock of 40 mM in DMSO and kept frozen at −20C (comparison between fresh and frozen IDX did not show any difference of activity). Dilutions were carried out in DMSO. Poly(I:C) and LPS were from Invivogen. Doxycycline hyclate (Sigma) was used at 1 µg/mL. The cGAS ligand ISD70 (also known as VACV-70) (8) was resuspended as follows: 5 µl of sense and 5 µl of antisense strands at 10 µg/µl were added to 90 µl PBS under sterile conditions, heated at 75° C. for 30 min, prior to letting cool down at room temperature and aliquoting (stock at 1 µg/1 µl). The ISDs were transfected at a concentration of 2.5 µg/ml at a ratio of 1 µg:1 µl with Lipofectamine 2000 in Opti-MEM (Thermo Fisher Scientific). ADU-S100 was purchased from MedChemExpress (#HY-12885) and resupended in RNase-DNase free water. The GSK compound is a human STING agonist recently reported (compound #3 from (1), referred to as GSK herein—kind gift from Cancer Therapeutics CRC, Australia). For infection with non-typeable *Haemophilus influenzae* (NTHi) (100 CFU/cell), THP-1 were pre-treated for 40 h with 50 ng/ml PMA. NTHi were grown as previously described (9).

Murine IP-10 production and IL-6 in supernatant of iBMMs and TC-1 was quantified using Mouse CXCL10/IP-10/CRG-2 Duo Set ELISA (R&D systems, #Dy466) and the IL6 OptE1A ELISA Kit mouse (BD Bioscience, #555240), respectively, according to the manufacturer's protocol. Similarly, human IP-10, TNF-α and IL-6 production was measured in cell supernatants using human IP-10 OptEIA ELISA kit (BD Biosciences, #555157), human OptEIA TNF-α kit (BD Bioscience, #555212) and human IL-6 OptEIA ELISA Set (BD Biosciences, #555220). Tetramethylbenzidine substrate (ThermoFisher Scientific) was used for quantification of the cytokines on a Fluostar OPTIMA (BMG LABTECH) plate-reader.

Cell transfections: HEK Sting cells were reverse transfected with 200 ng of IFNb-Luciferase reporter and 400 ng of cGAS-GFP overexpression vector, using 1.8 ul lipofectamine 2000 and ~600,000 cells, per well of a 96 well plate (as previously reported (8)). After 3 h, the cells were collected and aliquoted in 12 wells of a 96 well plate (for each well of a 6 well plate), and treated with indicated doses of IDX overnight, prior lysis in 40 ul of Glo lysis buffer the next day (Promega). Luciferase assays were carried out using the Promega Luciferase Assay System on a on a Fluostar OPTIMA (BMG LABTECH) plate-reader.

Viral assays: A total of 80 000 hTERT-BJ1 cells were seeded in 24-well plates three days after 10 uM IDX treatment, and left to adhere for several hours, prior to infection with Semliki forest virus (SFV) in complete DMEM (multiplicity of infection (MOI) of 2—as determined by plaque forming units in Vero cells) (each condition was carried out in biological triplicate), as previously described (10). The cells were rinsed 2 h after infection with fresh medium complemented with 2.5% FBS, and further incubated for 22 h. Virus-containing supernatants were collected at 24 h and series-diluted (10-fold dilutions) on 80% confluent Vero cells. After 48 h, surviving Vero cells were fixed with 10% formalin and stained with 0.1% crystal violet (w/v) in 20% ethanol, before several thorough $H_2O$ washes.

Western Blotting: Following lysis in RIPA buffer supplemented with complete mini protease inhibitor cocktail (Sigma #4693124001) and phosSTOP inhibitor (Sigma #4906845001), the samples were subjected to SDS-Page analyses, on NuPAGE 4%-12% Bis-Tris Protein Gels (Thermo Scientific) with MES or MOPS running buffer (Thermo Scientific), as previously reported (4). Anti-Sting (#13647), Phospho-Sting (#72971), TBK1 (#3013), phospho-TBK1 (#5483), IKKe (#3416), phospho-IKKe (#8766), IRF-3 (#4302), phosphor-IRF3 (#4947), p-65 (#4764), phospho-p-65 (#3033) antibodies were all from Cell Signalling. Anti-beta-Actin antibodies (#Ab49900) were from Abcam.

mRNA reverse transcription quantitative real-time PCR (RT-qPCR): Total RNA was purified from cells using the ISOLATE II RNA Mini Kit (Bioline). Random hexamer cDNA was synthesized from isolated RNA using the High-Capacity cDNA Archive kit (Thermo Fisher Scientific) according to the manufacturer's instructions. RT-qPCR was carried out with the Power SYBR Green Master Mix (Thermo Fisher Scientific) on the HT7900 and QuantStudio 6 RT-PCR system (Thermo Fisher Scientific). Each PCR was carried out in technical duplicate and mouse 18S was used as reference gene. Each amplicon was gel-purified and used to generate a standard curve for the quantification of gene expression (used in each run). Melting curves were used in each run to confirm specificity of amplification. The primers used in FIG. 16 were the following: Mouse Rsad2: mRsad2-FWD CTGTGCGCTGGAAGGTTT; mRsad2-REV ATTCAGGCACCAAACAGGAC; Mouse 18S: mRn18s-FWD GTAACCCGTTGAACCCCATT; mRn18s-REV CCATCCAATCGGTAGTAGCG; Mouse Ifih1: mIfih1-FWD TCTTGGACACTTGCTTCGAG; mIfih1-REV TCCTTCTGCACAATCCTTCTC; Mouse Ifit1: mIfit1-RT-FWD GAGAGTCAAGGCAGGTTTCT; mIfit1-RT-REV TCTCACTTCCAAATCAGGTATGT.

In vivo experiments: Trex1-mutant mice (7-8 week old) were injected daily with 200 ul of a freshly prepared PBS solution of IDX intraperitoneally (at 192 ug/ml). Control mice were injected with PBS only. Mice were culled after 10 days and sera analyses by LEGENDplex bead-based immunoassay (as per manufacturer's instructions), while spleens were collected and lysed for RNA purification. Transgenic mice that selectively over-express active TGF-β1 in the lung following doxycycline (Dox) administration (8 week old) were treated with Dox for 48 hrs, prior to infection with influenza A virus. Mice were subsequently treated with 250 ul of a freshly prepared PBS solution of IDX intraperitoneally (at 384 ug/ml) on day 1 and day 2 post infection, and the animals culled on day 3. Dox was injected daily throughout the duration of the infection. Bronchial Alveolar Lavages (BALs) were performed with two successive lavages of 800 uL, and analysed by IL-6 ELISA.

Figure 1:
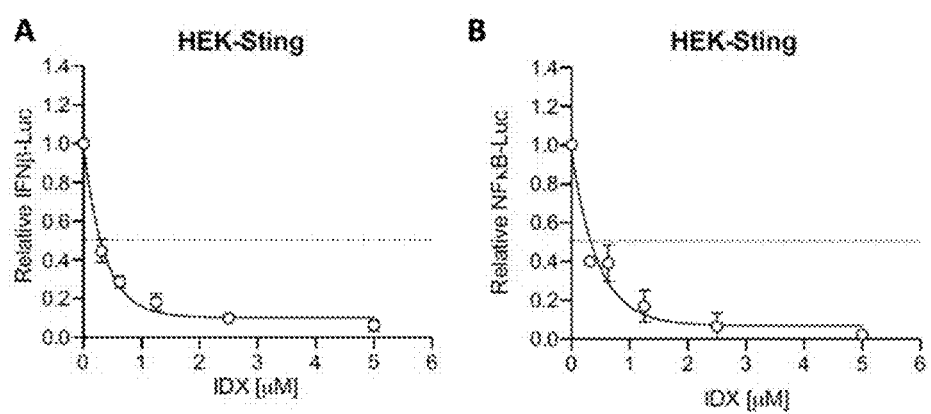
FIG. 1: Human HEK cells constitutively expressing mouse STING-mCherry were co-transfected with cGAS-GFP and an interferon (IFN)beta-luciferase (A) or an NF-κB-Luc reporter (B) reporter for 3 h prior to being treated overnight with indicated concentration of IDX (in equal volume of DMSO). Firefly luciferase was quantified the next day. Data shown are averaged from 2 (B) or 3 (A) independent experiments in biological triplicate, relative to DMSO only condition control (±SEM).

Results:

The inventors tested idronoxil (IDX) in HEK-Sting cells overexpressing cGAS-GFP and an interferon-β (IFN-β)-luciferase reporter, at different doses, and identified that Idronoxil (IDX) is a potent inhibitor of IFN-β-luciferase (FIG. 1).

Figure 2:
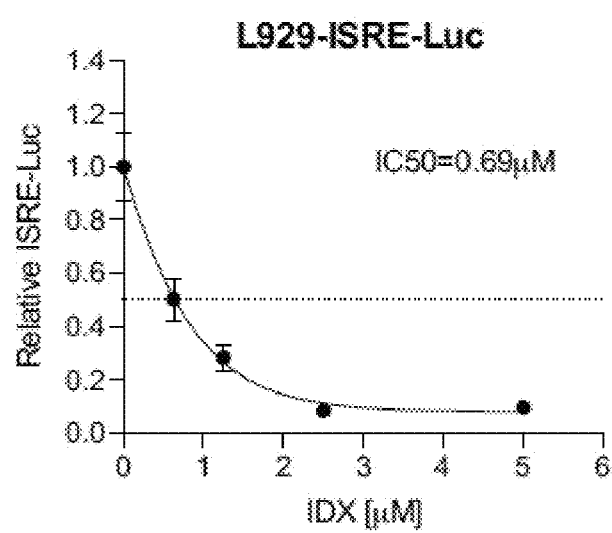
FIG. 2: Mouse L929 cells stably expressing an IFN-stimulated responsive element (ISRE)-luciferase reporter were pre-treated for 1 h with indicated doses of IDX, prior an 8 h stimulation with 20 ug/ml DMXAA. Cells were lysed and firefly luciferase was quantified at the end of the experiment. Data shown are averaged from 2 independent experiments in biological triplicate, relative to DMXAA and DMSO only condition control (±SEM).
Figure 3:
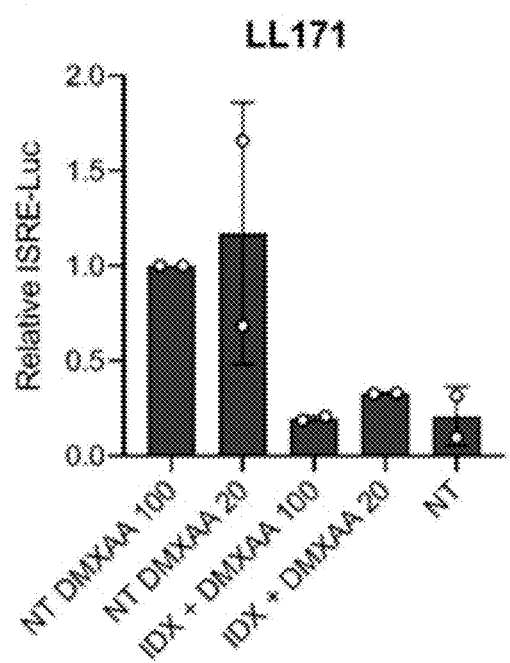
FIG. 3: Similar to FIG. 2, the L929 cells were pre-treated with 2.5 uM of IDX, prior to stimulation with increasing concentrations of DMXAA for 8 h. Luciferase assays were carried out at 8 hours. Data were normalised to DMSO+DMXAA only condition, and are shown as averages from 3 independent experiments (conducted with biological replicate), ±SD. Each point represents the mean data for each independent experiment; the column represents the mean of the experiments.

To determine whether IDX could inhibit STING signalling more directly, mouse L929 cells stably expressing an IFN-stimulated-responsive luciferase (ISRE-Luc) were pre-treated with IDX at various doses for 1 h, prior to DMXAA stimulation for 8 h (FIG. 2). DMXAA is an activator of mouse STING (11). In agreement with the data in HEK STING, IDX strongly inhibited DMXAA induced ISRE-Luc, even at 0.625 uM. This effect was not due to a competitive binding with DMXAA to STING, since increasing DMXAA to 100 ug/ml did not change the efficacy of the inhibition (FIG. 3).

The inhibitory effect of IDX on IL-6 is not surprising as it is well known that the molecule IDX is closely related in structure to genistein, which inhibits NF-κB signalling. The IDX induced reduction in IL-6 production may therefore be the result from an inhibition of the NF-κB signalling branch downstream of STING. Using mouse L929 cells stably expressing an interferon (IFN)-stimulated responsive element (ISRE)-Luciferase construct referred to as LL171 cells (2) and stimulated with the murine STING agonist DMXAA, the inventors speculated that the DMXAA-induced IFN-β production and downstream ISRE-Luciferase expression would only be minimally impacted by IDX if it selectively acted on NF-κB signalling. Surprisingly, pre-treatment of the cells for 1 hour with IDX prior to 8 hours stimulation with DMXAA strongly impaired ISRE-Luc induction in a dose-dependent manner (FIG. 3A). In addition, increasing concentrations of DMXAA to up to 100 μg/mL did not reverse the inhibition by IDX (FIG. 3B). The direct inhibition of DMXAA sensing by IDX and its effect on the IFN-β branch of STING indicated that IDX may act as a direct inhibitor of mouse STING.

To determine whether the effect of IDX on STING extended to humans, a hyperactive STING mutant (R284S) that constitutively activates NF-kB and IRF3 upon expression was tested. Stable undifferentiated THP-1 cells expressing STING R284S under a Doxycycline-inducible promoter were treated for 1 h with 2.5 uM IDX prior to overnight STING induction and IP-10 ELISA (FIG. 4). This experiment confirmed the capacity of IDX to significantly reduce the IRF3 branch induced by STING R284S expression—confirming its efficacy against human STING. In agreement with this, overnight inducible expression of STING R284S in immortalised mouse bone marrow macrophages led to a strong IP-10 induction that was blunted by IDX pre-treatment (FIG. 5).

Figure 6:
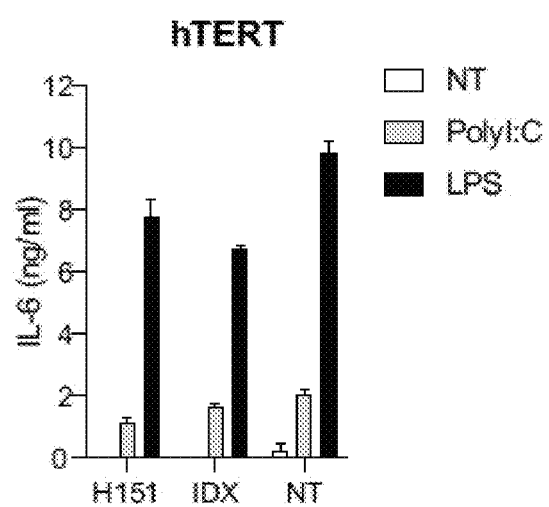
FIG. 6: Human TERT immortalised foreskin fibroblasts were treated for 1 h with 2.5 uM IDX prior to stimulation with polyI:C (20 ug/ml) or LPS (100 ng/ml) for 7 h. IL-6 levels were measured in the supernatants by ELISA. Data shown are from a single experiment in biological triplicate and representative of two independent experiments (±SEM).

To determine the specificity of IDX on STING signalling, human hTERT immortalised foreskin fibroblasts which have functional TLR4 (LPS) and TLR3 (PolyI:C) responsiveness were tested. Pre-treatment of the cells with 2.5 uM IDX or the STING inhibitor H151 prior to 7 h stimulation with LPS or PolyI:C, only modestly reduced IL-6 production (indicative of moderate activity on NF-kB signalling in this model). This suggests that in short term experiments such that in L929 cells, the effect of IDX seen on the ISRE-luciferase reporter is predominantly due to inhibition of the IRF3 branch rather than the NF-kB branch of STING signalling. (FIG. 6).

The inventors have demonstrated that IDX has the ability to significantly lower levels of IL-6 and interferons by affecting both the NF-κB and IRF3 pathways through its inhibitory effect on the STING pathway.

DNA damage in virally infected cells operates via the same immune-sensing mechanisms.

It is known that DNA damage could lead, in certain cells, to the accumulation of cytoplasmic DNA that subsequently engages the cGAS-STING pathway. Whilst the treatment of fibroblasts expressing the SV40T large antigen with low dose topoisomerase I inhibitor (camptothecin—CPT), leads to cGAS-STING activation, primary mouse embryonic fibroblasts do not display this response, indicating that SV40T somehow potentiates cytoplasmic leakage of damaged DNA (2). Other viral oncogenes, similar to SV40T, also potentiate cGAS-STING engagement by damaged DNA, such as TC-1 cells derived from lung cells of C57BLJ6 mice immortalized with HPV-16 E6/E7 oncogenes and transformed with H-ras (5). In both SV40T-expressing and TC-1 cells stimulated with CPT for more than 24 hours, the inventors have demonstrated a significant induction of IL-6 production (FIG. 7). Without wishing to be bound by theory, the inventors postulate that this response was cGAS and STING-dependent since CPT treatment in the presence of aspirin or H-151, which inhibits cGAS (12) and STING (13), respectively, strongly reduced IL-6 production (FIG. 7). Treatment with low dose IDX significantly reduced the CPT-induced IL-6 production.

To further test the signalling pathway, the effect of CPT and IDX on human prostate cancer PC-3 cells, which have been reported to have functional cGAS-STING and constitutive levels of cytoplasmic DNA (14), was utilised. Interestingly, whilst IL-6 levels were significantly increased by CPT within 24 hours, this was not inhibited by aspirin—indicating that in these cells the response to damaged DNA is independent of cGAS (FIG. 8). However, CPT-induced IL-6 levels were dampened by H-151, suggestive of STING dependency. Similar to the TC-1 cell model, IDX significantly reduced the CPT-induced IL-6 production in this model.

Further confirmation of IDX's ability to inhibit IL-6 expression was determined in two human osteosarcoma cancer cell lines (HOS and MG63), where CPT induced robust levels of IL-6 in a STING-dependent manner (relying on H151 inhibition), and IDX strongly reduced IL-6 levels (FIGS. 9A and 9B).

Importantly, IL-6 production upon transfection of immunostimulatory DNA (ISD) that activates cGAS-STING, was also decreased in MG-63 cells pre-treated for 48 hours with IDX (FIG. 10), showing the ability of IDX to significantly lower levels of IL-6 via the STING pathway extends beyond CPT-driven DNA damage.

To further determine the direct activity of IDX on STING, immortalised mouse bone marrow derived macrophages were stimulated with DMXAA for 1, 2 or 3 hours in the presence of IDX (FIG. 11). The cell lysates were analysed by Western blotting using specific total or phospho-antibody against STING, TBK1, IRF3, and p-65 (FIG. 11). In support of its inhibitory activity on downstream STING signaling, IDX decreased phosphorylation of TBK1 and IRF3 and also STING itself. Importantly, STING activation was also revealed by a shift in size of total STING, which was attenuated by IDX (with two clear bands visible over the 3-hour period). While these effects could all be dependent on TBK1 inhibition by IDX, the inventors also observed decreased p-65 phosphorylation that was not dependent on TBK1 in this cell system (4). These results therefore support a direct action of IDX on STING activation itself, rather than TBK1.

The inventors confirmed IDX's ability to block the action of established potent STING agonists in human THP-1 cells. IDX pre-treatment of the cells for 1 hour strongly inhibited IP-10 production driven by ADU-S100 (cGAMP synthetic analogue) and a synthetic STING agonist (1) (FIG. 12A). In addition, the inventors measured IFNβ levels produced by the THP-1 after stimulation with the synthetic STING agonist. IDX significantly blunted IFNβ production by ~50% in this model, as measured by specific IFNβ ELISA (FIG. 12B). The capacity to blunt activation of STING by such potent ligands confirms the strong inhibitory effect of IDX on STING signaling.

To assess the capacity of IDX to impact lung bacterial infections involved with STING signaling, the inventors tested the impact of non-typeable *Haemophilus influenzae*

(NTHi) induced inflammation in THP-1 cells pre-treated with IDX (15). Lung NTHi is the most frequent factor associated with acute exacerbation of chronic obstructive pulmonary disease (AECOPD). These experiments (FIG. 13) confirmed the potent anti-inflammatory effect of IDX pre-treatment. Similarly, incubation of human hTERT fibroblasts for 72 hours with 10 µM IDX (which had little impact on cell proliferation), did not sensitize cells to SFV infection (FIG. 14).

These results indicate that IDX does not sensitise cells to RNA virus infection (noting that SFV is very sensitive to IFN production generated upon sensing of dsRNA made by the virus).

In addition, the inventors sought to confirm the inhibition of STING signalling in primary cells given that the data generated so far was limited to cell lines.

First, the inventors tested the effect of 2.5 µM IDX pre-treatment on human peripheral blood mononuclear cells (PBMCs) from two donors, stimulated with the human synthetic STING agonist. Similar to the observations in human monocytic cells (THP-1), IDX pre-treatment reduced IL-6 and TNFα production as measured by cytokine ELISA (FIG. 15).

Next, the inventors tested the effect of overnight incubation with 1.25 and 2.5 µM IDX on primary bone marrow derived macrophages from Trex1 mutant mice. These mice have a single-based mutation in Trex1 leading to a premature stop codon (Q169X) and aberrant accumulation of cytoplasmic DNA, resulting in basal engagement of the cGAS-STING pathway, similar to that reported in Trex1-deficient mice (16). In agreement with the other data presented herein, the inventors observed a dose-dependent inhibition of 3 interferon stimulated genes (Ifit1, Ifih1, Rsad2) with IDX treatment of the cells, consistent with the inhibition of basal Sting signalling in these primary cells (FIG. 16).

Further, the inventors investigated the capacity of IDX to reduce basal STING signalling in Trex1-mutant mice. The mice were injected each day with 2 mg/kg of IDX in suspension in PBS for 10 days, and sera as well as spleen RNA were collected. Analyses of serum TNFα levels indicated a decrease with IDX compared to PBS controls, and expression of several interferon stimulated gene (Ifi44, Ifih1, Rsad2 and Isg15) were also decreased in the spleen (FIG. 17), noting a significant decreased was seen with Isg15. These experiments support that IDX limits basal STING seen in Trex1-mutant mice.

Finally, the inventors investigated the capacity of IDX to reduce the production of lung pro-inflammatory cytokines in the context of a mouse model of influenza A virus (IAV) infection where the inflammation is exacerbated by lung specific TGF-b expression (17). The mice were injected daily with 5 mg/kg of IDX in suspension from day 1 after infection with IAV, until day 3 when bronchial alveolar lavages were performed. While IL-6 levels were induced by IAV, therapeutic use of IDX post infection was able to significantly reduce the production IL-6 in the infected animals, confirming its potential to curb pathogen driven lung inflammation (FIG. 18).

Herein IDX has been demonstrated to modulate STING signalling, leading to reduced production of cytokines that are associated with adverse inflammatory responses that are observed in some patients infected with COVID-19.

Through its inhibitory effect of STING signalling, IDX has the potential to block the production of a broad range of cytokines including type I interferons (IFN-s) and pro-inflammatory cytokines such as IL-6 and TNF-α. This broader approach differs from current strategies aiming at blocking single cytokine receptors such as IL-6 receptors.

IDX may therefore be used to treat inflammation associated with infection, wherein the individual is identified as having, or suspected of having, early stage organ damage caused by the inflammation. There is a unique opportunity to use IDX in these infected patients with severe inflammation symptoms to reduce the time spent within the hospital system, the pathology associated with COVID-19 infection and inflammation and patient mortality.

REFERENCES

1. Ramanjulu, J. M., Pesirdis, G. S., Yang, J., Concha, N., Singhaus, R., Zhang, S.-Y., Tran, J.-L., Moore, P., Lehmann, S., Eberl, H. C. et al. (2018) Design of amidobenzimidazole STING receptor agonists with systemic activity. *Nature*, 564, 439-443.
2. Pépin, G., Nejad, C., Ferrand, J., Thomas, B. J., Stunden, H. J., Sanij, E., Foo, C.-H., Stewart, C. R., Cain, J. E., Bardin, P. G. et al. (2017) Topoisomerase 1 Inhibition Promotes Cyclic GMP-AMP Synthase-Dependent Antiviral Responses. *mBio*, 8.
3. Ablasser, A., Schmid-Burgk, J. L., Hemmerling, I., Horvath, G. L., Schmidt, T., Latz, E. and Hornung, V. (2013) Cell intrinsic immunity spreads to bystander cells via the intercellular transfer of cGAMP. *Nature*, 503, 530-534.
4. Balka, K. R., Louis, C., Saunders, T. L., Smith, A. M., Calleja, D. J., D'Silva, D. B., Moghaddas, F., Tailler, M., Lawlor, K. E., Zhan, Y. et al. (2020) TBK1 and IKKE Act Redundantly to Mediate STING-Induced NF-κB Responses in Myeloid Cells. *Cell Reports*, 31, 107492.
5. Lin, K.-Y., Guamieri, F. G., Staveley-O'Carroll, K. F., Levitsky, H. I., August, J. T., Pardoll, D. M. and Wu, T.-C. (1996) Treatment of Established Tumors with a Novel Vaccine That Enhances Major Histocompatibility Class II Presentation of Tumor Antigen. *Cancer Research*, 56, 6.
6. Ferrand, J. and Gantier, M. P. (2016) Assessing the Inhibitory Activity of Oligonucleotides on TLR7 Sensing. 1390, 79-90.
7. Gantier, M. P. (2013) Strategies for Designing and Validating Immunostimulatory siRNAs. 942, 179-191.
8. Pépin, G., De Nardo, D., Rootes, C. L., Ullah, T. R., Al-Asmari, S. S., Balka, K. R., Li, H.-M., Quinn, K. M., Moghaddas, F., Chappaz, S. et al. (2020) Connexin-Dependent Transfer of cGAMP to Phagocytes Modulates Antiviral Responses. *mBio*, 11.
9. Palaniyar, N., King, P. T., Sharma, R., O'Sullivan, K., Selemidis, S., Lim, S., Radhakrishna, N., Lo, C., Prasad, J., Callaghan, J. et al. (2015) Nontypeable *Haemophilus influenzae* Induces Sustained Lung Oxidative Stress and Protease Expression. *Plos One*, 10, e0120371.
10. Pépin, G., Nejad, C., Thomas, B. J., Ferrand, J., McArthur, K., Bardin, P. G., Williams, B. R. G. and Gantier, M. P. (2017) Activation of cGAS-dependent antiviral responses by DNA intercalating agents. *Nucleic Acids Research*, 45, 198-205.
11. Gao, P., Ascano, M., Zillinger, T., Wang, W., Dai, P., Serganov, Artem A., Gaffney, Barbara L., Shuman, S., Jones, Roger A., Deng, L. et al. (2013) Structure-Function Analysis of STING Activation by c[G(2',5')pA(3',5')p] and Targeting by Antiviral DMXAA. *Cell*, 154, 748-762.
12. Dai, J., Huang, Y.-J., He, X., Zhao, M., Wang, X., Liu, Z.-S., Xue, W., Cai, H., Zhan, X.-Y., Huang, S.-Y. et al. (2019) Acetylation Blocks cGAS Activity and Inhibits Self-DNA-Induced Autoimmunity. *Cell*, 176, 1447-1460.e1414.

13. Haag, S. M., Gulen, M. F., Reymond, L., Gibelin, A., Abrami, L., Decout, A., Heymann, M., van der Goot, F. G., Turcatti, G., Behrendt, R. et al. (2018) Targeting STING with covalent small-molecule inhibitors. *Nature*, 559, 269-273.
14. Ho, Samantha S. W., Zhang, Wendy Y. L., Tan, Nikki Yi J., Khatoo, M., Suter, Manuel A., Tripathi, S., Cheung, Florence S. G., Lim, Weng K., Tan, Puay H., Ngeow, J. et al. (2016) The DNA Structure-Specific Endonuclease MUS81 Mediates DNA Sensor STING-Dependent Host Rejection of Prostate Cancer Cells. *Immunity*, 44, 1177-1189.
15. Lu, C., Zhang, X., Ma, C., Xu, W., Gan, L., Cui, J., Yin, Y. and Wang, H. (2018) Nontypeable *Haemophilus influenzae* DNA stimulates type I interferon expression via STING signaling pathway. *Biochimica et Biophysica Acta (BBA)—Molecular Cell Research*, 1865, 665-673.
16. Gray, E. E., Treuting, P. M., Woodward, J. J. and Stetson, D. B. (2015) Cutting Edge: cGAS Is Required for Lethal Autoimmune Disease in the Trex1-Deficient Mouse Model of Aicardi-Goutibres Syndrome. *The Journal of Immunology*, 195, 1939-1943.
17. Lee, C. G., Cho, S. J., Kang, M. J., Chapoval, S. P., Lee, P. J., Noble, P. W., Yehualaeshet, T., Lu, B., Flavell, R. A., Milbrandt, J. et al. (2004) Early Growth Response Gene 1-mediated Apoptosis Is Essential for Transforming Growth Factor β1-induced Pulmonary Fibrosis. *Journal of Experimental Medicine*, 200, 377-389.

The invention claimed is:

1. A method of treating inflammation associated with an infection in an individual having an activated STING pathway, the method comprising or consisting of the steps of:
    administering a therapeutically effective amount of idronoxil, or pharmaceutically acceptable salt, ester, amide, and/or prodrug thereof to the individual;
    wherein administration period consists of the period from early stage organ damage to prior to late stage organ damage caused by inflammation associated with infection, wherein the inflammation is associated with an activated STING pathway,
    thereby treating the inflammation, wherein the inflammation is associated with an activated STING pathway.

2. The method according to claim 1, wherein the individual is identified as having at least one symptom of early stage organ damage caused by inflammation associated with infection, wherein the inflammation is associated with an activated STING pathway.

3. The method according to claim 1, wherein the individual has not been administered idronoxil, or pharmaceutically acceptable salt, ester, amide, and/or prodrug thereof at the onset of infection.

4. The method according to claim 1, wherein the individual has not been administered idronoxil, or pharmaceutically acceptable salt, ester, amide, and/or prodrug thereof at the onset of inflammation.

5. The method according to claim 1, wherein the infection is caused by a virus.

6. The method according to claim 5, wherein the virus is selected from: coronavirus, influenza, parainfluenza, respiratory syncytial virus (RSV), adenovirus, cytomegalovirus (CMV), Epstein-Barr virus (EBV), varicella zoster virus (VZV), dengue virus, rhinovirus, Herpes simplex virus and enteroviruses.

7. The method according to claim 6 wherein the virus is a coronavirus or influenza.

8. The method according to claim 7, wherein the virus is severe acute respiratory syndrome coronavirus 2 (SARS-CoV-2).

9. The method according to claim 1, wherein the infection is caused by a bacterium.

10. The method according to claim 9, wherein the bacterium is selected from: *Streptococcus* spp., *Escherichia coli*, *Pseudomonas aeruginosa*, *Haemophilus influenza*, *Klebsiella pneumoniae*, and *Acinetobacter baumannii* and *Neisseria meningitidis*.

11. The method according to claim 10, wherein the individual is diagnosed with or suspected of having a viral infection.

12. The method according to claim 2, wherein the symptom of early stage organ damage is selected from: abnormal levels of one or more cytokines or inflammatory biomarkers, abnormal levels of clotting factors, abnormal levels of troponin I, abnormal levels of alanine aminotransferase, abnormal levels of blood urea nitrogen, abnormal levels of creatinine, abnormal levels of procalcitonin, abnormal levels of lactic dehydrogenase, elevated body temperature, elevated heart rate, elevated respiratory rate, abnormal lymphocyte cell count, abnormal neutrophil cell count, abnormal platelet cell count, low blood pressure, hypoxemia, tissue hypoxia, hypoperfusion, redness and swelling around a wound, low urine volume, dizziness or faintness, pale, discoloured or mottled skin, slurred speech, rigors, malaise, fatigue, anorexia, myalgia, arthralgia, nausea, vomiting, headache, rash, vomiting, diarrhoea, widened pulse pressure, increased cardiac output (early), potentially diminished cardiac output (late), hypofibrinogenemia ±bleeding, azotemia, transaminitis, hyperbilirubinemia, mental status changes, confusion, delirium, word finding difficulty or frank aphasia, hallucinations, tremor, dysmetria, altered gait, seizures and combinations thereof.

13. The method according to claim 2, wherein the individual is identified as having, or suspected of having, at least 2, 3, 4, 5, or 6 symptoms of early stage organ damage.

14. The method according to claim 12, wherein the one or more cytokines or inflammatory biomarkers is selected from: interleukin-1 (IL-1), interleukin-6 (IL-6), interleukin-8 (IL-8), interleukin-11 (IL-11), interleukin-12 (IL-12), interleukin-17 (IL-17), interleukin-18 (IL-18), interleukin-37 (IL-37), IP-10, tumour necrosis factor-alpha (TNF-α), interferon-gamma (IFN-γ), granulocyte-macrophage colony stimulating factor (GM-CSF), transforming growth factor-beta (TGF-β), interleukin-2 receptor (IL-2R), interleukin-4 (IL-4), interleukin-10 (IL-10), interleukin-13 (IL-13), interferon-alpha (IFN-α), interferon-beta (IFN-β), monocyte chemoattractant protein-1 (MCP-1 or CCL2), procalcitonin (PCT), C-reactive protein (CRP), C-C Motif Chemokine Ligand 5 (CCL5 or RANTES), β-2-microglobulin (β-2M), serum ferritin, D-dimer, cyclic guanosine monophosphate-adenosine monophosphate (cGAMP), and combinations thereof.

15. The method according to claim 14, wherein the one or more cytokines or inflammatory biomarkers is selected from: IL-1β, IL-2R, IL-6, IL-8, IL-10, IL-12, IP-10, TNF-α, MCP-1, PCT, CRP, β-2M, serum ferritin, D-dimer, cGAMP, CCL5 (RANTES), IFN-α, IFN-β, IFN-γ and combinations thereof.

16. The method according to claim 14, wherein the individual is identified as having abnormal levels of at least 2, 3, 4, 5, or 6 cytokines or inflammatory biomarkers.

17. The method according to claim 2, wherein the symptom of early stage organ damage is D-dimer levels greater than 1 μg/mL.

18. The method according to claim 1, wherein the individual is not identified, diagnosed, or suspected of having, a symptom of late stage organ damage associated with inflammation caused by infection.

19. The method according to claim 1, further comprising administration of an antibiotic, optionally including intravenous fluids.

\* \* \* \* \*